(12) United States Patent
Wang et al.

(10) Patent No.: US 12,419,811 B2
(45) Date of Patent: Sep. 23, 2025

(54) HYDROGEL DRUG DELIVERY COMPOSITION

(71) Applicant: Board of Regents of the University of Nebraska, Lincoln, NE (US)

(72) Inventors: Dong Wang, Omaha, NE (US); Yosif Almoshari, Abha (SA); Rongguo Ren, Omaha, NE (US); Ningrong Chen, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 174 days.

(21) Appl. No.: 17/604,659

(22) PCT Filed: Apr. 20, 2020

(86) PCT No.: PCT/CN2020/085549
§ 371 (c)(1),
(2) Date: Oct. 18, 2021

(87) PCT Pub. No.: WO2020/211859
PCT Pub. Date: Oct. 22, 2020

(65) Prior Publication Data
US 2022/0218571 A1 Jul. 14, 2022

Related U.S. Application Data

(60) Provisional application No. 62/835,542, filed on Apr. 18, 2019.

(51) Int. Cl.
| | |
|---|---|
| A61K 47/10 | (2017.01) |
| A61K 6/20 | (2020.01) |
| A61K 6/69 | (2020.01) |
| A61K 9/00 | (2006.01) |
| A61K 9/06 | (2006.01) |
| A61P 31/00 | (2006.01) |

(52) U.S. Cl.
CPC ............ *A61K 6/20* (2020.01); *A61K 6/69* (2020.01); *A61K 9/0063* (2013.01); *A61K 9/06* (2013.01); *A61K 47/10* (2013.01); *A61P 31/00* (2018.01)

(58) Field of Classification Search
None
See application file for complete search history.

(56) References Cited

U.S. PATENT DOCUMENTS

| | | | | |
|---|---|---|---|---|
| 4,780,320 A | * | 10/1988 | Baker ................... | A61K 6/30 424/493 |
| 2007/0258915 A1 | * | 11/2007 | Kielbania .............. | A61L 9/145 424/53 |
| 2009/0074886 A1 | | 3/2009 | Bennett et al. | |
| 2013/0149355 A1 | | 6/2013 | Roberts et al. | |

FOREIGN PATENT DOCUMENTS

| | | |
|---|---|---|
| WO | 2005039485 A2 | 5/2005 |
| WO | WO-2010006192 A1 * | 1/2010 ........... A61K 31/045 |
| WO | 2013142817 A2 | 9/2013 |
| WO | 2016196400 A1 | 12/2016 |
| WO | 2018073599 A1 | 4/2018 |

OTHER PUBLICATIONS

Neves et al (Promotion of natural tooth repair by small molecule GSK3 antagonists. Scientific Reports. 7:39654 (2017) p. 1-13) (Year: 2017).*
Vasikaran (Bisphosphonates: an overview with special reference to alendronate. Ann Clin Biochem 2001; 38: 608-623) (Year: 2001).*
Takahashi-Yanaga F. Activator or inhibitor? GSK-3 as a new drug target. Biochemical Pharmacology. Jul. 2013;86(2):191-199.
Wang D, Miller SC, Kope?ková P, Kope?ek J. Bone-targeting macromolecular therapeutics. Advanced Drug Delivery Reviews. May 2005;57(7):1049-1076.
Wang FS, Ko JY, Weng LH, Yeh DW, Ke HJ, Wu SL. Inhibition of glycogen synthase kinase-3? attenuates glucocorticoid-induced bone loss. Life Sciences. Nov. 2009;85(19-20):685-692.
Wang H, Brown J, Martin M. Glycogen synthase kinase 3: a point of convergence for the host inflammatory response. Cytokine. Feb. 2011;53(2):130-140.
Wang X, Jia Z, Almoshari Y, Lele SM, Reinhardt RA, Wang D. Local application of pyrophosphorylated simvastatin prevents experimental periodontitis. Pharmaceutical Research. Aug. 2018;35(8):164.
Wang Y, Huang WC, Wang CY, Tsai CC, Chen CL, Chang YT, Kai JI, Lin CF. Inhibiting glycogen synthase kinase?3 reduces endotoxaemic acute renal failure by down?regulating inflammation and renal cell apoptosis. British Journal of Pharmacology. Jul. 2009;157(6):1004-1013.
Whittle BJ, Varga C, Pósa A, Molnár A, Collin M, Thiemermann C. Reduction of experimental colitis in the rat by inhibitors of glycogen synthase kinase?3 ?. British Journal of Pharmacology. Mar. 2006;147(5):575-582.
Williams RC, Jeffcoat MK, Howell TH, Reddy MS, Johnson HG, Hall CM, Goldhaber P. Ibuprofen: an inhibitor of alveolar bone resorption in beagles. Journal of Periodontal Research. Jul. 1988;23(4):225-229.
Winter HH. Can the gel point of a cross?linking polymer be detected by the G?-G? crossover? Polymer Engineering and Science. Dec. 1987;27(22):1698-1702.
Xie J, Méndez JD, Méndez-Valenzuela V, Aguilar-Hernández MM. Cellular signalling of the receptor for advanced glycation end products (RAGE). Cellular Signaling. Nov. 2013;25(11):2185-2197.

(Continued)

*Primary Examiner* — Jake M Vu
(74) *Attorney, Agent, or Firm* — Robert C. Netter, Jr.; Dann, Dorfman, Herrell & Skillman

(57) ABSTRACT

Disclosed is a hydrogel drug delivery composition comprising a therapeutic agent and a poloxamer, wherein the poloxamer is modified to be capable of adhering to a surface of bones or teeth, and wherein the poloxamer is modified by pyrophosphate, bisphosphonates, acidic peptides or tetracycline and its derivatives.

19 Claims, 8 Drawing Sheets

(56) References Cited

OTHER PUBLICATIONS

Almoshari, Y.H. et al., Development of Local Drug Delivery Systems for Periodontal Disease, https://digitalcommons.unmc.edu/etd/3631, Apr. 30, 2019 (Apr. 30, 2019), pp. 1-2.

Bai, S.B. et al., Research progress of bisphosphonates as bone targeting ligands, Journal of Ningxia Medical University, vol. 39, No. 10, Oct. 31, 2017 (Oct. 31, 2017), pp. 1234-1238.

Zhang, Y. et al., Statins, bone metabolism and treatment of bone catabolic diseases, Pharmacological Research, vol. 88, Jan. 7, 2014 (Jan. 7, 2014), pp. 53-61.

International Search Report and Written Opinion for International Application No. PCT/CN20/85549, filed Apr. 20, 2021, mailed Jul. 20, 2020.

Adamowicz K, Wang H, Jotwani R, Zeller I, Potempa J, Scott DA. Inhibition of GSK3 abolishes bacterial-induced periodontal bone loss in mice. Molecular Medicine. Aug. 2012;18(8):1190-1196.

Akash MS, Rehman K, Li N, Gao JQ, Sun H, Chen S. Sustained delivery of IL-1Ra from pluronic F127-based thermosensitive gel prolongs its therapeutic potentials. Pharmaceutical Research. Dec. 1, 2012;29(12):3475-3485.

Arioka M, Takahashi-Yanaga F, Sasaki M, Yoshihara T, Morimoto S, Hirata M, Mori Y, Sasaguri T. Acceleration of bone regeneration by local application of lithium: Wnt signal-mediated osteoblastogenesis and Wnt signal-independent suppression of osteoclastogenesis. Biochemical Pharmacology. Aug. 2014;90(4):397-405.

Bai X, Gao M, Syed S, Zhuang J, Xu X, Zhang XQ. Bioactive hydrogels for bone regeneration. Bioactive Materials. Dec. 2018;3(4):401-417.

Bercea M, Darie RN, Nita LE, Morariu S. Temperature Responsive Gels Based on Pluronic F127 and Poly(vinyl alcohol). Industrial & Engineering Chemistry Research. Mar. 2011;50(7):4199-4206.

Bolon B, Morony S, Cheng Y, Hu YL, Feige U. Osteoclast numbers in Lewis rats with adjuvant-induced arthritis: identification of preferred sites and parameters for rapid quantitative analysis. Veterinary Pathology. Jan. 2004;41(1):30-36.

Bradley AD, Zhang Y, Jia Z, Zhao G, Wang X, Pranke L, Schmid MJ, Wang D, Reinhardt RA. Effect of simvastatin prodrug on experimental periodontitis. Journal of Periodontology. May 2016;87(5):577-582.

Chen F, Jia Z, Rice KC, Reinhardt RA, Bayles KW, Wang D. The development of dentotropic micelles with biodegradable tooth-binding moieties. Pharmaceutical Research. Nov. 2013;30(11):2808-2817.

Deshmukh M, Singh Y, Gunaseelan S, Gao D, Stein S, Sinko PJ. Biodegradable poly (ethylene glycol) hydrogels based on a self-elimination degradation mechanism. Biomaterials. Sep. 2010;31(26):6675-6684.

Diniz IM, Chen C, Xu X, Ansari S, Zadeh HH, Marques MM, Shi S, Moshaverinia A. Pluronic F-127 hydrogel as a promising scaffold for encapsulation of dental-derived mesenchymal stem cells. Journal of Materials Science: Materials in Medicine. Mar. 2015;26(3):153.

Dumortier G, Grossiord JL, Agnely F, Chaumeil JC. A review of poloxamer 407 pharmaceutical and pharmacological characteristics. Pharmaceutical Research. Dec. 2006;23(12):2709-2728.

Fakhar-ud-Din, Khan GM. Development and characterisation of levosulpiride-loaded suppositories with improved bioavailability in vivo. Pharmaceutical Development and Technology. Jan. 2019;24(1):63-69.

Fukuda T, Kokabu S, Ohte S, Sasanuma H, Kanomata K, Yoneyama K, Kato H, Akita M, Oda H, Katagiri T. Canonical Wnts and BMPs cooperatively induce osteoblastic differentiation through a GSK3 ?-dependent and ?-catenin-independent mechanism. Differentiation. Jul. 2010;80(1):46-52.

Georgiou KR, King TJ, Scherer MA, Zhou H, Foster BK, Xian CJ. Attenuated Wnt/?-catenin signalling mediates methotrexate chemotherapy-induced bone loss and marrow adiposity in rats. Bone. Jun. 2012;50(6):1223-1233.

Gibson-Corley KN, Olivier AK, Meyerholz DK. Principles for valid histopathologic scoring in research. Veterinary Pathology. Nov. 2013;50(6):1007-1015.

Giuliano E, Paolino D, Fresta M, Cosco D. Mucosal Applications of Poloxamer 407-Based Hydrogels: An Overview. Pharmaceutics. Sep. 2018;10(3):E159.

Greenstein G. Local drug delivery in the treatment of periodontal diseases: assessing the clinical significance of the results. Journal of Periodontology. Apr. 2006;77(4):565-578.

Herrera D, Sanz M, Jepsen S, Needleman I, Roldán S. A systematic review on the effect of systemic antimicrobials as an adjunct to scaling and root planing in periodontitis patients. Journal of Clinical Periodontology. Dec. 2002;29:136-159.

Huang P, Yan R, Zhang X, Wang L, Ke X, Qu Y. Activating Wnt/ ?-catenin signaling pathway for disease therapy: Challenges and opportunities. Pharmacology & Therapeutics. Apr. 2019;196:79-90.

Huang WC, Lin YS, Wang CY, Tsai CC, Tseng HC, Chen CL, Lu PJ, Chen PS, Qian L, Hong JS, Lin CF. Glycogen synthase kinase?3 negatively regulates anti?inflammatory interleukin?10 for lipopolysaccharide?induced INOS/NO biosynthesis and RANTES production in microglial cells. Immunology. Sep. 2009;128(1 Pt 2):e275-e286.

Jain, M.K. & Ridker, P.M. Anti-Inflammatory Effects of Statins: Clinical Evidence and Basic Mechanisms. Nature Reviews Drug Discovery, 2005. 4, p. 977-87.

Jia Z, Wang X, Wei X, Zhao G, Foster KW, Qiu F, Gao Y, Yuan F, Yu F, Thiele GM, Bronich TK, O'Dell, JR, Wang D. Micelle-Forming Dexamethasone Prodrug Attenuates Nephritis in Lupus-Prone Mice without Apparent Glucocorticoid Side Effects. ACS Nano. Jul. 2018;12(8):7663-7681.

Jiang YY, Wen J, Gong C, Lin S, Zhang CX, Chen S, Cheng W, Li H. Bio alleviated compressive mechanical force? mediated mandibular cartilage pathological changes through Wnt/??catenin signaling activation. Journal of Orthopaedic Research. Apr. 2018;36(4):1228-1237.

Kahn M. Can we safely target the WNT pathway? Nature Reviews Drug Discovery. Jul. 2014;13(7):513-532.

Kennel KA, Drake MT. Adverse effects of bisphosphonates: implications for osteoporosis management. Mayo Clinic Proceedings Jul. 2009; 84(7):632-638.

Klamer G, Shen S, Song E, Rice AM, Knight R, Lindeman R, O'Brien TA, Dolnikov A. GSK3 inhibition prevents lethal GVHD in mice. Experimental Hematology. Jan. 2013;41(1):39-55.

Krause U, Harris S, Green A, Ylostalo J, Zeitouni S, Lee N, Gregory CA. Pharmaceutical modulation of canonical Wnt signaling in multipotent stromal cells for improved osteoinductive therapy. Proceedings of the National Academy of Sciences. Mar. 2010;107(9):4147-4152.

Kwon YJ, Yoon CH, Lee SW, Park YB, Lee SK, Park MC. Inhibition of glycogen synthase kinase-3? suppresses inflammatory responses in rheumatoid arthritis fibroblast-like synoviocytes and collagen-induced arthritis. Joint Bone Spine. May 2014;81(3):240-246.

Li Y, Cao J, Han S, Liang Y, Zhang T, Zhao H, Wang L, Sun Y. ECM based injectable thermo-sensitive hydrogel on the recovery of injured cartilage induced by osteoarthritis. Artificial Cells, Nanomedicine, and Biotechnology. Nov. 2018;46(sup2):152-160.

Low SA, Galliford CV, Yang J, Low PS, Kopec?ek J. Biodistribution of fracture-targeted gsk3? inhibitor-loaded micelles for improved fracture healing. Biomacromolecules. Sep. 2015;16(10):3145-3153.

Ma X, He Z, Han F, Zhong Z, Chen L, Li B. Preparation of collagen/hydroxyapatite/alendronate hybrid hydrogels as potential scaffolds for bone regeneration. Colloids and Surfaces B: Biointerfaces. Jul. 2016;143:81-87.

Martinez A, Castro A, Dorronsoro I, Alonso M. Glycogen synthase kinase 3 (GSK?3) inhibitors as new promising drugs for diabetes, neurodegeneration, cancer, and inflammation. Medicinal Research Reviews. Jul. 2002;22(4):373-384.

Monti D, Burgalassi S, Rossato MS, Albertini B, Passerini N, Rodriguez L, Chetoni P. Poloxamer 407 microspheres for orotransmucosal drug delivery. Part II: In vitro/in vivo evaluation. International Journal of Pharmaceutics. Nov. 2010;400(1-2):32-36.

(56) References Cited

OTHER PUBLICATIONS

Neves VC, Babb R, Chandrasekaran D, Sharpe PT. Promotion of natural tooth repair by small molecule GSK3 antagonists. Scientific Reports. Jan. 2017;7:39654.

Park DW, Jiang S, Liu Y, Siegal GP, Inoki K, Abraham E, Zmijewski Jw. GSK3 ?-dependent inhibition of AMPK potentiates activation of neutrophils and macrophages and enhances severity of acute lung injury. American Journal of Physiology-Lung Cellular and Molecular Physiology. Sep. 2014;307(10):L735-L745.

Pihlstrom BL, Michalowicz BS, Johnson NW. Periodontal diseases. The Lancet. Nov. 2005;366(9499):1809-1820.

Piters E, Boudin E, Van Hul W. Wnt signaling: a win for bone. Archives of Biochemistry and Biophysics. May 2008;473(2):112-116.

Polychronopoulos P, Magiatis P, Skaltsounis AL, Myrianthopoulos V, Mikros E, Tarricone A, Musacchio A, Roe SM, Pearl L, Leost M, Greengard P. Structural basis for the synthesis of indirubins as potent and selective inhibitors of glycogen synthase kinase-3 and cyclin-dependent kinases. Journal of Medicinal Chemistry. Feb. 2004;47(4):935-946.

Purcell PM, Boyd IW. Bisphosphonates and osteonecrosis of the jaw. Medical Journal of Australia. Apr. 2005;182(8):417-418.

Raja S, Byakod G, Pudakalkatti P. Growth factors in periodontal regeneration. International Journal of Dental Hygiene. May 2009;7(2):82-89.

Rangabhatla AS, Tantishaiyakul V, Boonrat O, Hirun N, Ouiyangkul P. Novel in situ mucoadhesive gels based on Pluronic F127 and xyloglucan containing metronidazole for treatment of periodontal disease. Iranian Polymer Journal. Nov. 2017;26(11):851-859.

Sanguineti R, Storace D, Monacelli F, Federici A, Odetti P. Pentosidine effects on human osteoblasts in vitro. Annals of the New York Academy of Sciences. Apr. 2008;1126(1):166-172.

Schett G, Stolina M, Bolon B, Middleton S, Adlam M, Brown H, Zhu L, Feige U, Zack DJ. Analysis of the kinetics of osteoclastogenesis in arthritic rats. Arthritis & Rheumatism: Official Journal of the American College of Rheumatology. Oct. 2005;52(10):3192-3201.

Sharma PK, Bhatia SR. Effect of anti-inflammatoiren Pluronic® F127: micellar assembly, gelation and partitioning. International Journal of Pharmaceutics. Jul. 2004;278(2):361-377.

Shellis RP, Addy M, Rees GD. In vitro studies on the effect of sodium tripolyphosphate on the interactions of stain and salivary protein with hydroxyapatite. Journal of dentistry. Apr. 1, 2005;33(4):313-24.

Song S, Ajani JA, Honjo S, Maru DM, Chen Q, Scott AW, Heallen TR, Xiao L, Hofstetter WL, Weston B, Lee JH. Hippo coactivator YAP1 upregulates SOX9 and endows esophageal cancer cells with stem-like properties. Cancer Research. Aug. 2014;74(15):4170-4182.

Extended European Search Report for European Application No. 20791279.1, filed Nov. 17, 2021 mailed May 8, 2023.

Jain et al., Recent approaches for the treatment of periodontitis, Drug Discovery Today, Elsevier, Amsterdam, NL, vol. 13, No. 21-22, Nov. 1, 2008, pp. 932-943.

Low et al., Targeting polymer therapeutics to bone, Advanced Drug Delivery Reviews, vol. 64, No. 12, Jan. 28, 2012, pp. 1189-1204.

* cited by examiner

HYDROGEL DRUG DELIVERY COMPOSITION

CROSS REFERENCE TO RELATED APPLICATIONS

This application is the U.S. national phase application of International Application No. PCT/CN2020/085549, filed on Apr. 20, 2020, which claims the priority to U.S. Provisional Application No. 62/835,542, filed on Apr. 18, 2019, the disclosures of both of which are hereby incorporated by reference in their entireties.

FIELD

The present invention relates to the field of drug delivery systems, specifically to a hydrogel drug delivery composition.

BACKGROUND

Oral disease is a very common disease in human. In most cases, the treatment of oral diseases only requires local medication, not systemic medication. For some patients, systemic medication may cause serious side effects. Moreover, systemic medication can easily lead to drug resistance in the body, reducing the efficacy of drugs. In addition, the oral environment is complex, and many factors affect the health of the oral cavity. For example, long-term use of antibiotics will destroy the normal flora of the oral cavity. Researchers have been looking for a delivery system that can effectively release drugs in the oral cavity in a targeted manner.

Periodontal disease is a prevalent and chronic inflammatory condition that affects the surrounding tissues of the teeth including gingiva, periodontal ligament, and alveolar bone resulting in pocket formation, mobility, bone loss, and eventually lead to the loss of tooth. In addition to the pathogenic bacterial population, the host immune response, which aims at protecting host tissues from bacterial aggression, also acts as a mediator of the periodontal damage[1]. Current treatment strategies aim at reducing bacterial load by mechanical therapy and administration of antimicrobial agents[2, 3]. Additionally, host modulation agents have been utilized to ameliorate inflammation and prevent disease progression[4, 5]. Their efficacy on halting the alveolar bone loss, which is the major destructive and non-reversible hallmark of periodontal disease, is limited. Therefore, there is an unmet clinical need to develop novel therapies that would prevent bone erosion and regenerate the lost alveolar bone.

Glycogen synthase kinase 3 beta (GSK3β) is a multi-tasking serine/threonine kinase with crucial roles in several physiological processes including inflammation and bone homeostasis. It has been shown to play a critical role in the host inflammatory response[6-8] and bone homeostasis[9] as a negative regulator, suggesting that inhibitors of GSK3β may provide therapeutic effects for inflammatory and bone metabolic diseases[10]. Particularly, a GSK3β inhibitor (SB216763) has been studied in periodontal disease and data confirmed its therapeutic benefits in preventing alveolar bone loss associated with periodontal disease[11]. During the last decade, several selective GSK-3B inhibitors have been synthesized and tested in clinical trials at various phases[12, 13]. In particular, 6-bromoindirubin-3'-oxime (BIO), a potent GSK3β inhibitor with an enzymatic IC50 of 5 nM, has exhibited anti-inflammatory[7, 8] and strong bone and teeth anabolic effects[14-20]. Due to the involvement of GSK3 in multiple physiological processes, however, systemic administration may cause serious adverse side effects (e.g., diarrhea, hypoglycemia, tumorigenesis)[21-23]. Hence, it is necessary to limit and restrict its biological action primarily at the intended site of action. Local delivery of BIO into the periodontal pocket will permit direct targeting of periodontal tissue, achieving high local concentrations along with minimizing systemic toxicities. However, the poor aqueous solubility and rapid clearance of BIO from the periodontal pockets post major challenges to its effective local delivery.

Statins, which were developed as 3-hydroxy-3-methylglutaryl (HMG)-CoA reductase inhibitors, have been widely used to treat cardiovascular diseases for decades. Mundy et al. reported that two statins, simvastatin (SIM) and lovastatin, have strong bone anabolic effects that were attributed to induction of the bone inducing factor bone morphogenic protein-2 (BMP-2). Later, statins are also noted for their anti-inflammatory effects[56]. Major efforts have been invested since then, attempting to validate this finding. The results remain controversial, however, in part due to the first-pass metabolism in the liver, which limits the amounts that reach bone when given orally and have prevented their clinical application to strengthen skeletal bones or treat periodontitis. Local applications of simvastatin are hindered by its poor water solubility (https://www.drugbank.ca/drugs/DB00641).

Thermoresponsive hydrogel formulations injected into the periodontal pocket would be a promising option for the local delivery of BIO or SIM to prevent the bony defects associated with periodontitis. Poloxamer 407 (Pluronic F127), a frequently used formulation excipient that has been approved by U.S. FDA for pharmaceutical applications, is a triblock amphiphilic copolymer consisting of a center block of polypropylene oxide flanked by two polyethylene oxide blocks (PEO101 PPO56 PEO101)[24-27]. It has been used extensively in controlled drug and cell delivery[28]. Its unique thermoresponsive gelation property in aqueous solutions (20-35% w/v) makes it an appealing carrier material for periodontal drug delivery and other similar applications[29, 30]. The amphiphilic F127 polymer enhances the solubility of hydrophobic drugs at room temperature by forming micelles. When exposed to physiological temperature, the polymer solution forms a hydrogel, holding encapsulated drugs in its collapsed micellar structure to provide sustained release kinetics. F127 is also known to be non-toxic and biocompatible[30]. The constant flow of crevicular fluid, the poor bone-adhesion and mechanical properties of F127 hydrogel, however, would significantly limit the bioavailability of the payload drug in the periodontal pocket.

Therefore, there is a need to improve binding of hydrogel to the hard tissues and develop a novel hydrogel drug delivery system for effective drug release in topical site.

SUMMARY

In one aspect, the present disclosure provides a drug delivery composition comprising a therapeutic agent and a poloxamer, wherein the poloxamer is modified to be capable of adhering to a surface of bones or teeth.

Poloxamers are nonionic triblock copolymers composed of a central hydrophobic chain of polyoxypropylene (poly(propylene oxide)) flanked by two hydrophilic chains of polyoxyethylene (poly(ethylene oxide)). Preferably, the poloxamer is modified by pyrophosphate, bisphosphonate, dopamine, acidic peptide, or tetracycline and a derivative thereof.

More preferably, the poloxamer is a pyrophosphorylated poloxamer or a mixture of poloxamer and pyrophosphorylated poloxamer.

In the embodiments of the present disclosure, wherein the poloxamer is selected from the group consisting of Pluronic L31, L35, F38, L42, L43, L44, L61, L62, L63, L64. P65, F68, L72, P75, F77, L81, P84, P85, F87, F88, L92, F98, L101, P103, P104, P105. F108, L121, L122, L123, F127, 10R5, 10R8, 12R3. 17R1, 17R2, 17R4, 17R8, 22R4, 25R1, 25R2, 25R4, 25R5, 25R8, 31R1, 31R2, 31R, and a mixture thereof, preferably, the poloxamer is poloxamer 407 (Pluronic F127);

the therapeutic agent includes anti-inflammatory compounds, bone anabolic compounds, bone antiresorptive compounds, anti-cancer compounds, statins, and anti-microbial compounds; preferably, the therapeutic agent is a GSK3-beta inhibitor or a statin.

The GSK3-beta inhibitors may be used in this invention are listed in Table 1.

TABLE 1

| Inhibitor | Structure |
|---|---|
| NP 031112 | 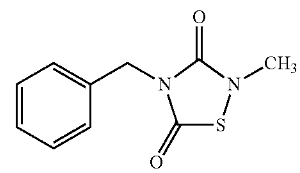 |
| GSK-3 Inhibitor XV | 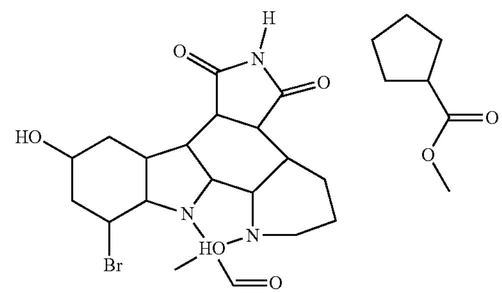 |
| CHIR98014 | CHIR98014 ($R_1$ = NO; $R_2$ = $NH_2$; $R_3$ = H)<br>CHIR99021 ($R_1$ = CN; $R_2$ = H; $R_3$ = $CH_3$) |
| 603281-31-8 | 7 R1 = Oipr; R2, R3 = H<br>8 R1 = Piperidinyl; R2, R3 = H<br>9 R1 = Piperidinyl; R2 = H, R3 = Me<br>10 R1 = Morpholinyl; R2, R3 = H<br>11 R1 = Dimethylaminyl; R2, R3 = H<br>12 R1 = Piperidinyl; R2 = F, R3 = H |

TABLE 1-continued

| Inhibitor | Structure |
|---|---|
| GSK-3 Inhibitor XXII, Compound A | 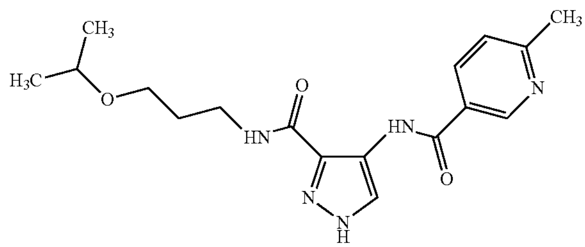 [SMILES: Cc1ccc(C(=O)Nc2c[nH]nc2C(=O)NCCCOC(C)C)cn1] |
| CT20026 | 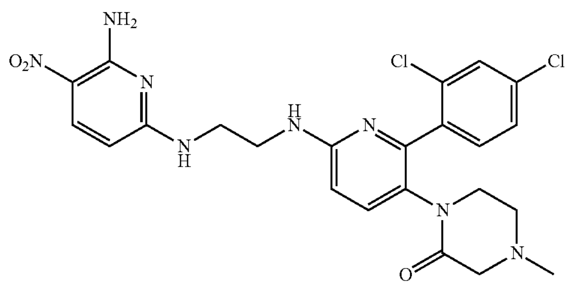 |
| Ro318220 | CT20025 |
| Alsterpaullone | 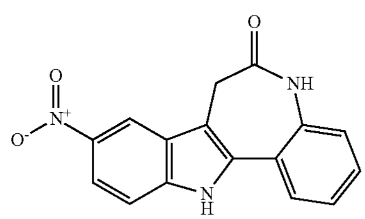 [SMILES: O=C1Cc2c([nH]c3ccc([N+](=O)[O-])cc23)-c2ccccc2N1] |
| AR28 | |
| 6-Bromoindirubin-3 oxime | 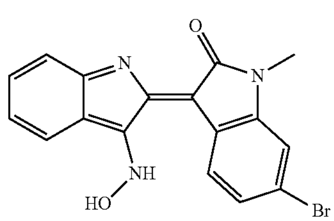 [SMILES: CN1C(=O)/C(=C2\N=c3ccccc3=C2NO)c2ccc(Br)cc21] |
| GSK-3 Inhibitor IX | 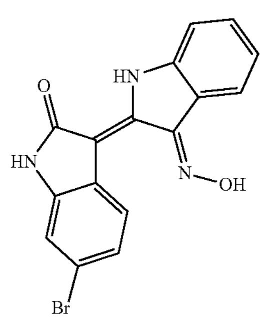 [SMILES: O=C1Nc2cc(Br)ccc2/C1=C1/Nc2ccccc2/C1=N\O] |

TABLE 1-continued

| Inhibitor | Structure |
| --- | --- |
| GSK-3 Inhibitor XVI | |
| CHIR99021 | CHIR98014 (R₁ = NO; R₂ = NH₂; R₃ = H) <br> CHIR99021 (R₁ = CN; R₂ = H; R₃ = CH₃) |
| Pyrazolopyridine 34 | 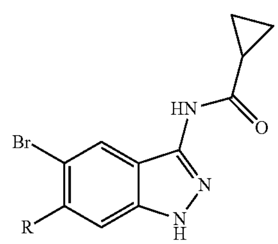 |
| Indirubin-3'-mono xime, 5-Iodo- | 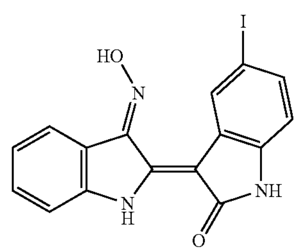 [SMILES: O=C1Nc2ccc(I)cc2/C1=C1/Nc2ccccc2/C1=N\O] |
| Hymenialdisine | 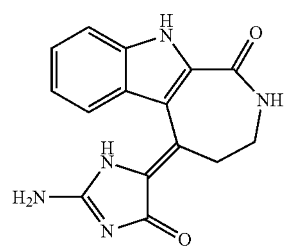 [SMILES: NC1=NC(=O)/C(=C2\CCNC(=O)c3[nH]c4ccccc4c32)N1] |
| 6-Bromoindirubin-3'-acetoxime | 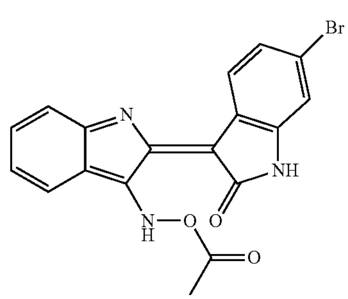 [SMILES: CC(=O)ONC1=c2ccccc2=N/C1=C1/C(=O)Nc2cc(Br)ccc21] |

TABLE 1-continued
| Inhibitor | Structure |
|---|---|
| CGP60474 | 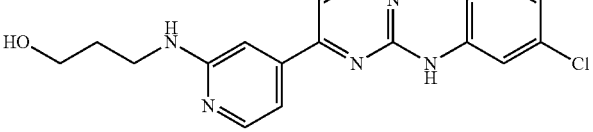 |
| GSK-3 Inhibitor X | 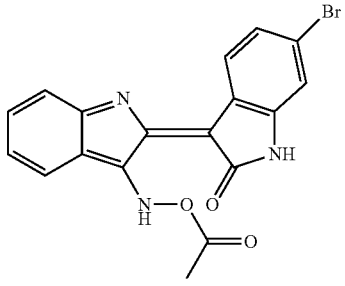 [SMILES: CC(=O)ONC1=c2ccccc2=N/C1=C1/C(=O)Nc2cc(Br)ccc21] |
| CG9 | |
| Compound 1A | 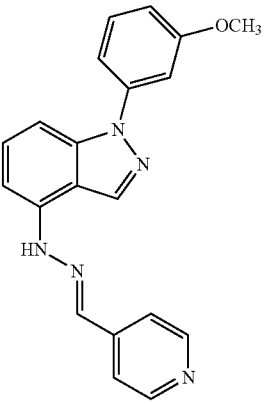 [SMILES: COc1cccc(-n2ncc3c(N/N=C/c4ccncc4)cccc32)c1] |
| Compound 5a | 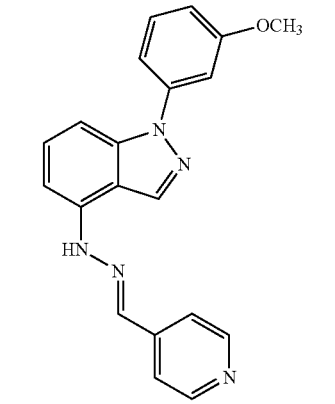 |
| AzakenPaullone | 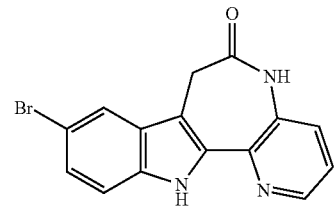 |
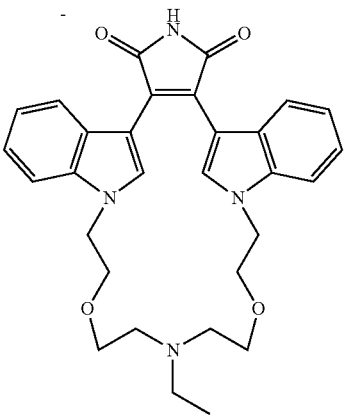 [SMILES: CCN1CCOCCn2cc(c3ccccc32)C2=C(C(=O)NC2=O)c2cn(c3ccccc23)CCOCC1]

TABLE 1-continued

| Inhibitor | Structure |
|---|---|
| Pyrazolopyridine 18 | 5-(2-fluorophenyl)-N-butanoyl-1H-pyrazolo[3,4-b]pyridin-3-amine |
| Indirubin-3-oxime | indirubin-3'-oxime with R substituent |
| Pyrazolopyridine 9 | 5-phenyl-N-(3-(dimethylamino)propanoyl)-1H-pyrazolo[3,4-c]pyridazin-3-amine |
| Kenpaullone | Paulione (R = H; X = C)<br>Kenpaulione (R = Br; X = C)<br>Alsterpaulione (R = NO₂; X = C)<br>Azakenpaulione (R = Br; X = N) |
| GSK-3 Inhibitor XIII | 2-phenyl-N-(5-methyl-1H-pyrazol-3-yl)quinazolin-4-amine |

TABLE 1-continued

| Inhibitor | Structure |
|---|---|
| GSK-3β Inhibitor XI | 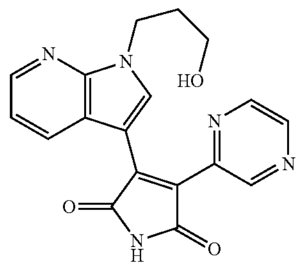 [SMILES: O=C1NC(=O)C(c2cn(CCCO)c3ncccc23)=C1c1cnccn1] |
| GSK-3β Inhibitor XII, TWS119 | 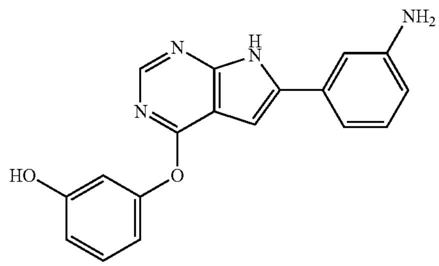 [SMILES: Nc1cccc(-c2cc3c(Oc4cccc(O)c4)ncnc3[nH]2)c1] |
| Compound 29 | 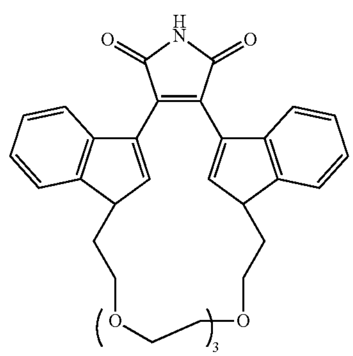 |
| GSK-3beta Inhibitor XXVI | 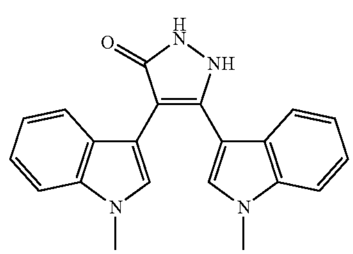 [SMILES: Cn1cc(-c2[nH][nH]c(=O)c2-c2cn(C)c3ccccc23)c2ccccc21] |
| Compound 46 | 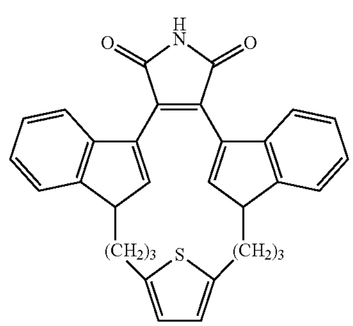 |

TABLE 1-continued

| Inhibitor | Structure |
|---|---|
| GSK-3β Peptide Inhibitor, Cell-permeable | Myr-N-Gly-Lys-Glu-Ala-Pro-Pro-Ala-Pro-Pro-Gln-Ser(PO₃H)-Pro-NH₂ |
| GSK3β Inhibitor XIX, IM-12 | 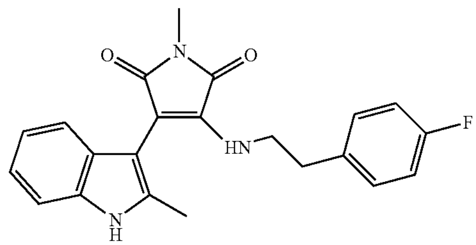 [SMILES: Cc1[nH]c2ccccc2c1C1=C(NCCc2ccc(F)cc2)C(=O)N(C)C1=O] |
| AZD2858 | |
| Indirubin-3'-mono xime-5-sulphonic Acid | 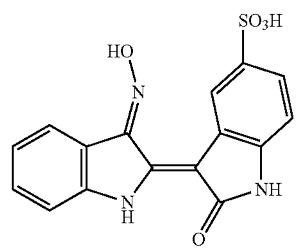 [SMILES: O=C1Nc2ccc(S(=O)(=O)O)cc2/C1=C1/Nc2ccccc2/C1=N\O] |
| Staurosporine | 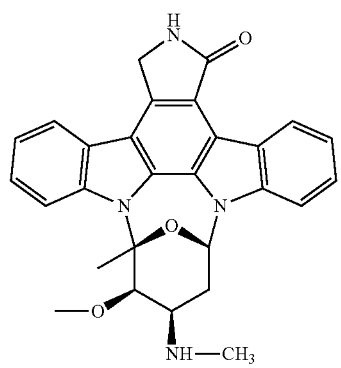 [SMILES: CN[C@@H]1C[C@H]2O[C@](C)([C@@H]1OC)n1c3ccccc3c3c4c(c5c6ccccc6n2c5c31)C(=O)NC4] |
| GSK-3 Inhibitor IX, Control, MeBIO | |
| ARA014418 | 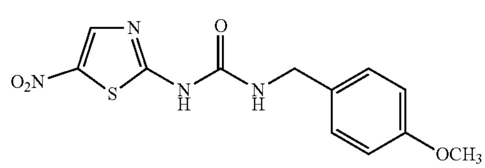 [SMILES: COc1ccc(CNC(=O)Nc2ncc([N+](=O)[O-])s2)cc1] |
| GSK-3β Inhibitor VIII | 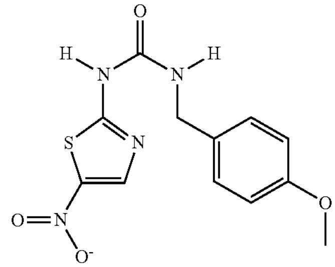 |

TABLE 1-continued
| Inhibitor | Structure |
|---|---|
| SB216763 | 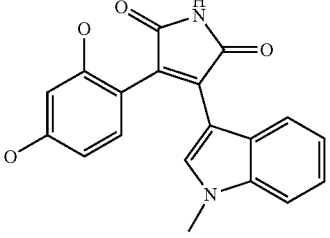 |
| SB415286 | 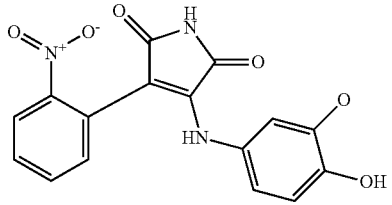 [SMILES: O=C1NC(=O)C(c2ccccc2[N+](=O)[O-])=C1Nc1ccc(O)c(O)c1] |
| GSK-3β Peptide Inhibitor | H-Lys-Glu-Ala-Pro-Pro-Ala-Pro-Pro-Gln-Ser(PO$_3$H)-Pro-NH$_2$ |
| I5 | 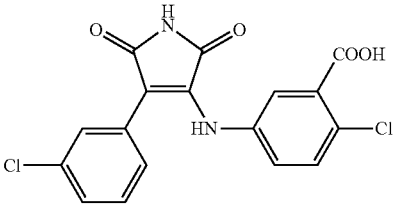 |
| GF109203x | 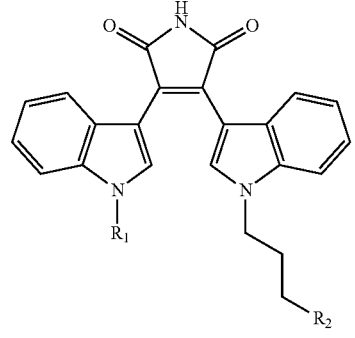 |
I9203x
H; R$_2$ = N(CH$_3$)$_2$]
8220

TABLE 1-continued
| Inhibitor | Structure |
|---|---|
| Compound 8b | 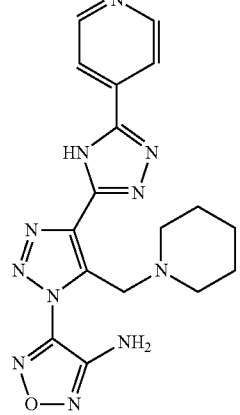 |
| SU9516 | 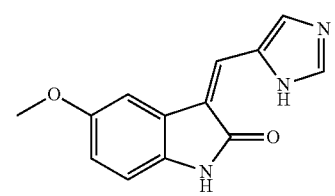  R = 2-furyl) |
| GSK-3 Inhibitor II | 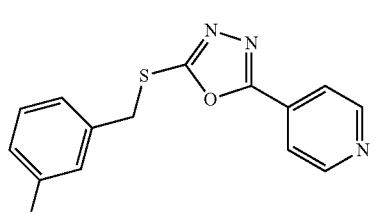 |
| Flavopiridol | 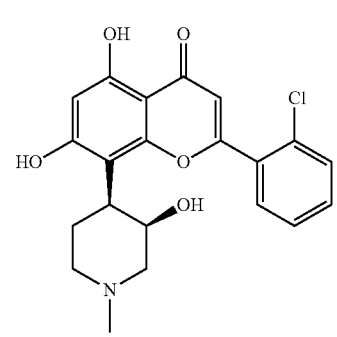 [SMILES: CN1CC[C@@H](c2c(O)cc(O)c3c(=O)cc(-c4ccccc4Cl)oc23)[C@@H](O)C1] |
| GSK-3β Inhibitor VII | 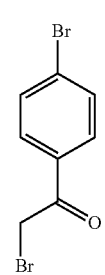 |

TABLE 1-continued

| Inhibitor | Structure |
|---|---|
| Isogranulatimide | 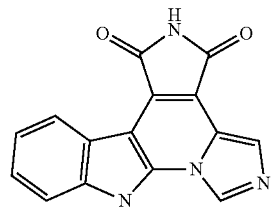 [SMILES: O=C1NC(=O)c2c1c1c3ccccc3[nH]c1n1cncc21] |
| Aloisine A | Aloisine A<br>[R₁ = OH; R₂ = (CH₂)₃CH₃]<br>Aloisine B<br>[R₁ = Cl; R₂ = CH(CH₃)₂] |
| TDZD8 | 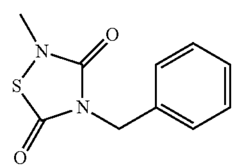 |
| Aloisine B | Aloisine A<br>[R₁ = OH; R₂ = (CH₂)₃CH₃]<br>Aloisine B<br>[R₁ = Cl; R₂ = CH(CH₃)₂] |
| Compound 12 | 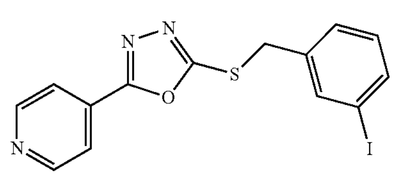 [SMILES: Ic1cccc(CSc2nnc(-c3ccncc3)o2)c1] |
| Compound 17 | 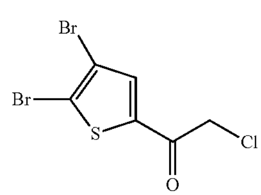 [SMILES: O=C(CCl)c1cc(Br)c(Br)s1] |
| Compound 1 | 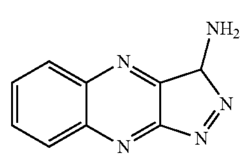 [SMILES: NC1N=Nc2nc3ccccc3nc21] |

TABLE 1-continued

| Inhibitor | Structure |
|---|---|
| GSK-3β Inhibitor VI | (structure: 4,5-dibromo-2-(2-chloroacetyl)thiophene) |
| Lithium | |
| GSK-3β Inhibitor I | (structure: 3-(benzyl)-4-methyl-1,2,4-thiadiazolidine-3,5-dione derivative) |
| Beryllium | |
| Zinc | |

In one embodiment of the present disclosure, wherein the GSK3-beta inhibitor is selected from the compounds listed in Table 1, such as indirubin and its derivatives, lithium, beryllium, zinc, and a mixture thereof; preferably, the GSK3-beta inhibitor is 6-bromoindirubin-3'-oxime, lithium, or zinc.

The statins may be used in this invention include atorvastatin (Lipitor), fluvastatin (Lescol, Lescol XL), lovastatin (Mevacor, Altoprev), pravastatin (Pravachol), rosuvastatin (Crestor), simvastatin (Zocor), and pitavastatin (Livalo).

Preferably, the composition is in a form of hydrogel and the hydrogel is thermosensitive.

In another aspect, the present disclosure provides a method of manufacturing the drug delivery composition comprising,
  subjecting the poloxamer to tosylation reaction to synthesize tosylated poloxamer;
  subjecting the tosylated poloxamer to pyrophosphorylation to obtain pyrophosphorylated poloxamer; and
  dissolving the therapeutic agent in the pyrophosphorylated poloxamer to obtain a hydrogel containing the drug delivery composition.

In another aspect, the present disclosure provides a method of treating an oral disease comprising administering the drug delivery composition in situ at a topical site to a subject in need thereof.

Preferably, the topical site is a tooth and the oral disease is a dental disease, more preferably periodontitis. The composition is capable of releasing the therapeutic agent to treat the oral disease over a period of at least 2 days, and the composition is adherent only to the topical site.

DETAILED DESCRIPTION

Figure 1:
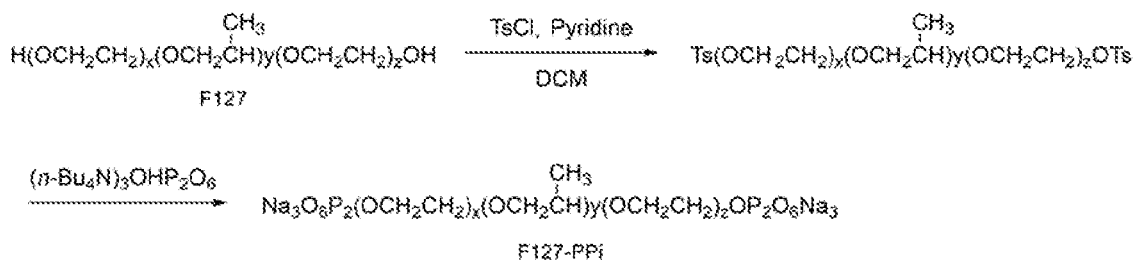
FIG. 1 shows the synthesis of pyrophosphorylated Pluronic F127 (F127-PPi).

The embodiments of the present disclosure will be described in detail below with reference to the embodiments. However, a person having ordinary skill in the art will understand that the following embodiments are merely to illustrate present disclosure and are not intended to limit the scope of the disclosure. For those embodiments in which specific conditions are not specified, they were carried out according to the conventional conditions or the conditions recommended by the manufacturer. For those used reagents or instruments of which the manufacturers are not indicated, they were all commercially available conventional products.

Example 1

Materials and Reagents

Pluronic F127 and pyrophosphate were purchased from Sigma-Aldrich (Saint Louis in MO, USA). BIO was synthesized according to literature[31]. Dense Ceramic Hydroxyapatite discs (0.5" diameter and 0.08" Thick) were obtained from Clarkson Chromatography Products, Inc. (South Williamsport, PA USA). Mouse osteoblast MC3T3-L1 cells were acquired from ATCC (Manassas, VA, USA). Fetal bovine serum (FBS, BenchMark™) was acquired from Gemini BenchMark (West Sacramento, CA). Minimum Essential Media (alpha-MEM), and trypsin-EDTA were purchased from GIBCO (Grand Island, NY, USA). Cell Counting Kit-8 (CCK-8) was bought from Dojindo Molecular Technologies, Inc. (Rockville, MD USA). All other solvents and reagents, if not specified, were acquired from either Acros Organics (Morris Plains, NJ, USA) or Fisher Scientific (Pittsburgh, PA, USA).

Synthesis of Pyrophosphorylated Pluronic F127 (F127-PPi)
Synthesis of Tosylated Pluronic F127

Pluronic F127 (1.0 g, 0.079 mmol) and 4-toluenesulfonyl chloride (151 mg, 0.79 mmol) were dissolved in dry dichloromethane. Pyridine (62 μL, 0.79 mmol) was then added and the resulting solution was stirred for 24 hr at 21° C. After adding dichloromethane (80 mL), the resulting solution was washed with HCl (1 M, 20 mL) and brine (80 mL×2). After washing, the organic phase was separated and dried over MgSO$_4$. The solution was filtered, concentrated and the residue was purified on a LH-20 column to produce 922 mg of the final product, yield: 90%. $^1$H NMR (CDCl$_3$, 500 MHz) δ ppm 7.78 (d, J=3.0 Hz, 4H), 7.33 (d, J=3.0 Hz 4H), 4.14 (t, J=5.0 Hz, 4H), 3.77 (t, J=4.5 Hz, 8H), 3.59-3.55 (m, 872H), 3.50-3.44 (m, 142H), 3.38 (m, 65H), 2.44 (s, 6H), 1.12 (t, J=5.0 Hz, 195H); $^{13}$C NMR (CDCl$_3$, 125 MHZ) δ ppm 144.7, 133.0, 129.8, 127.9, 75.5, 75.4, 75.1, 73.4, 73.0, 72.9, 72.7, 69.2, 68.7, 21.6, 17.5, 17.3.

Synthesis of Pyrophosphorylated Pluronic F127

The tosylated Pluronic F127 (1.0 g, 0.077 mmol) and tris(tetra-n-butylammonium) hydrogen diphosphate [(n-Bu$_4$N)$_3$(HO)P$_2$O$_6$] (0.31 mmol, 280 mg) were dissolved in dry acetonitrile. The solution was stirred at 21° C. until the starting materials completely disappeared (~3 hr, monitored by TLC). After removal of the solvents, the residue was dissolved in water (20 mL) and dialyzed (MWCO=12-14 kDa) against NaCl solution (0.1 mol/L) overnight to exchange tetrabutyl ammonium to sodium. The resulting solution was then dialyzed against distilled water to remove the excessive NaCl. The resulting solution was then lyophilized to obtain 859 mg of the final pyrophosphorylated Pluronic F127 (F127-PPi) product, yield: 85%. The synthesis path is shown in FIG. 1.

$^1$H NMR (CDCl$_3$, 500 MHz) δ ppm 4.16 (t, J=5.0 Hz, 4H), 3.78 (t, J=4.5 Hz, 8H), 3.59-3.54 (m, 872H), 3.50-3.44 (m, 142H), 3.39-3.36 (m, 65H), 1.13 (t, J=5.0 Hz, 195H); $^{13}$C NMR (CDCl$_3$, 125 MHZ) δ ppm 75.5, 75.4, 75.1, 73.4, 73.0, 72.9, 72.8, 72.7, 70.6, 17.5, 17.3; $^{31}$P NMR (202.5 MHz, CDCl$_3$): δ (ppm)=−7.70 (d, J=20.2 Hz), −7.91 (d, J=20.2 Hz).

To determine the PPi content, F127-PPi was hydrolyzed in 1 M HCl for 2 hr at 100° C. to release the phosphate. After removal of F127 with chloroform extraction, an equal volume of 1 M HCl solution containing 0.5% (w/v) ammonium molybdate and 2% (w/v) ascorbic acid was added. The samples were incubated at 37° C. for 2 hr then their absorbance at 820 nm was measured using a UV spectrometer[49]. Eighty percent terminal hydroxyl groups of F127 was found to has been pyrophosphorylated.

Preparation of BIO-loaded Thermoresponsive Hydrogel

PF127 hydrogel formulations with predetermined polymer concentrations (20, 25 and 30% w/v) were prepared by mixing F127-PPi and F127 at different ratio (0:100, 25:75, 50:50, 75:25, 100:0% w/w). Briefly, the desired amount of F127-PPi and F127 was dissolved in PBS (pH 7.4) with stirring in an ice-water bath (~4° C., to prevent gelation) until a clear solution (PF127) was obtained and then stored at 4° C. overnight. BIO was then dissolved in the polymer solutions by continuous stirring at 4° C., the obtained solutions were filtered through 0.8 μm filter syringes.

Binding Potential to Model Bone (Hydroxyapatite, or HA)

To assess the binding potential of the formulated hydrogels to hydroxyapatite or HA, which constitute the main inorganic component of bone and teeth, an in vitro binding study was done using HA discs. Briefly, polymer solutions (25% w/v) were prepared, containing 100 μM of BIO, with different ratios of F127-PPi and F127 (0:100, 25:75, 50:50, 75:25, and 100:0% w/w) to optimize binding affinity. Hydrogels (1 mL) were formed on HA disc placed in plastic wells at 37° C., and the hydrogels were allowed to stabilize for 15 min. After that, HA discs, on which hydrogels are formed, were inverted with temperature maintained at 37° C. by keeping the inverted hydrogels inside the water bath (37° C.). The binding time of hydrogel to HA disc was measured. The binding experiment was performed in triplicate. Based on this study, one formulation was selected for all subsequent experiments.

Evaluation of BIO's Solubility in PF127 and F127 Solutions

The aqueous solubility of BIO in PF127 and F127 solutions was assessed in this experiment. The solubility values of BIO were measured at dissolution equilibrium after adding the BIO to the PF127 and F127-containing media for a predetermined period of time, as reported previously[32]. Specifically, an excessive amount of BIO was added to different concentrations of PF127 or F127 solutions in microcentrifuge tubes. The suspensions were mixed on a rotor at 4° C. for 48 hr to achieve dissolution equilibrium. At 4° C., the suspensions were centrifuged at 2,000 rpm for 5 min to settle the undissolved drug to the bottom of the microcentrifuge tube. The supernatants were then filtered through 0.8 μm syringe filters to obtain the saturated BIO solutions. A UV SpectraMax M2 spectrophotometer (Molecular Devices, Sunnyvale, CA, USA) was used to measure BIO concentrations at 260 nm.

In Vitro Release of BIO from Hydrogel

The release rate of the physically entrapped BIO from PF127 hydrogels (20, 25, and 30% w/v), was studied by a membrane-less experiment, as reported previously[33-35]. Briefly, samples of 1 mL of polymer solutions containing 0.5 mg of BIO were transferred into screw cap tubes and incubated in a water bath at 37° C. until the gels were formed. After gelation, 2 mL of phosphate-buffered saline (PBS; pH 7.4) containing 0.5% Tween 80 pre-equilibrated at 37° C. were gently laid over the surface of the hydrogels and incubated in a water bath at 37° C. with continuous gentle shaking. To measure the release of BIO, release medium (2 mL) were taken at regular time intervals and replaced with an equal volume of pre-equilibrated fresh releasing buffer. The concentration of BIO was determined by measuring the absorbance at 260 nm using a Molecular Device's Spectramax M2 (Sunnyvale, CA, USA). The release study was performed in triplicate.

In Vitro Hydrogel Erosion

The erosion time of PF127 hydrogel formulations (20, 25, and 30% w/v) was determined by performing the weight remaining (%) experiment, as reported by others[33-35]. Briefly, samples of 1 mL of polymer solutions were transferred into screw cap tubes and incubated in a water bath at 37° C. until the gels were formed. After gelation, the original weight of the hydrogel samples was measured as ($W_0$). Subsequently, 2 mL of PBS (pH 7.4) pre-equilibrated at 37° C. were gently laid over the surface of the hydrogels and incubated in a water bath at 37° C. with continuous gentle shaking. The weight of remaining hydrogels ($W_1$) was measured at regular time intervals after completely blotting off the buffer. Erosion study was performed in triplicate. Weight remaining (%) was calculated as:

$$\text{Weight remaining}(\%) = \frac{(W_0 - W_t)}{W_0} \times 100$$

Biocompatibility of PF127 Hydrogel

The impact of selected PF127 hydrogel formulation (25% w/v of mixed F127-PPi and F127, 50:50% w/w) and F127 hydrogel (25% w/v) (with or without BIO) on cell viability were assessed using CCK-8 assay. The BIO concentration in all BIO-containing formulations is 100 nM. Briefly, mouse preosteoblast MC3T3-L1 cell line was cultured in cell culture medium (alpha-MEM) with 10% (v/v) FBS and 1% (v/v) Penicillin/Streptomycin. The cells were incubated to 90% confluence under standard conditions at 37° C. in humidified atmosphere with 5% $CO_2$. The hydrogels were extracted in alpha-MEM at 37° C. for 24 hr according to the ISO Standard 10993-12 [34, 35] The ratio between the surface area of the hydrogels and the volume of medium was 1.25 $cm^2$/mL. Undiluted extracts were used for the assay. Cells were grown in 96 well plates ($1 \times 10^4$ cells/well) and incubated for 24 hr at 37° C. The cells were then treated with either media only, PF127 extract, PF127-BIO extract, F127 extract, F127-BIO extract, or free BIO, and the plates were incubated at 37° C. for 24 and 48 hr. At each follow-up time point, CCK-8 reagent (10 μL) was added to each well and further incubated for 4 hr at 37° C. The absorbance was measured at 450 nm using a Molecular Device's Spectramax M2 microplate reader (Sunnyvale, CA, USA).

Gelation and Viscosity Studies

Gelation temperature was determined by measuring the storage modulus (G') and loss modulus (G") of samples in the temperature sweep mode[36, 37]. Solutions with w/v concentrations ranging between 20 and 40% were prepared as described above. Each sample was uniformly loaded between the Peltier plate of the rheometer (TA Instruments AR1500ex) and a 60 mm-diameter, 1° cone geometry at 3° C. The linear viscoelastic region of each sample was predetermined at 45° C. by using the oscillation amplitude function, and the following condition was chosen: strain of 0.1%, and angular frequency of 1 rad/s. Then, the G' and G" of each sample were measured for the temperature range from 3° C. to 45° C. by using the oscillation temperature sweep function of the rheometer (heating step: 1° C., soak time: 2 min for each temperature increase). The gelation temperature of each sample was determined as the temperature when G' and G" become equal.

The viscosity of gel phase was also investigated at constant temperature by flow sweep[30] (37° C., shear rate from 1 to 100 $s^{-1}$) using the rheometer and a 25 mm-diameter parallel plate. Samples were dispensed on the Peltier plate of the rheometer, heated to 37° C. and maintained at 37° C. for 15 min to reach thermal stability before isothermally tested.

The Therapeutic Efficacy of BIO-Containing Hydrogels on a Rat Model of Experimental Periodontitis Ten-month-old female Sprague Dawley rats (retired breeders, Envigo) were acclimated for one week prior to experiment. The animals (n=48) were randomly assigned into the following groups (Table 1): healthy control, experimental periodontitis (EP) treated with saline, EP treated with 25% w/v of mixed F127-PPi and F127 hydrogel (50:50% w/w, containing 100 μM of BIO) (PF127-BIO), EP treated with 25% w/v of F127 hydrogel (containing 100 μM of BIO) (F127-BIO), EP treated with 25% w/v of PF127 hydrogel, and EP treated with free BIO (100 μM). Using silk ligatures, the experimental periodontitis was induced as described previously[32, 38]. Briefly, rats were first anesthetized in an isoflurane chamber with a 1% to 4% isoflurane in 100% $O_2$. After taking the body weight, the rats were positioned with a nose cone supplied with 0.5% to 2% isoflurane and 100% $O_2$ to maintain anesthesia during the entire procedure. To induce experimental periodontitis, a 4-0 silk ligature was gently tightened subgingivally around the maxillary $2^{nd}$ molars (M2). Following ligature placement, different treatments (10 μL) were locally delivered between the maxillary $1^{st}$ molar (M1) and $2^{nd}$ molar (M2) once each week for 3 weeks. After one week, the ligatures were removed. All animals were euthanized at week 4. The entire palate including all three molars was dissected and fixed in 10% formalin prior to micro-CT and histological analyses. All animals-related experiments were approved by the Institutional Animal Care and Use Committee (IACUC) of the University of Nebraska Medical Center (UNMC).

TABLE 2

| Group | # of animals | Week 1 | Week 2 | Week 3 | Week 4 |
|---|---|---|---|---|---|
| Untreated healthy control (Con+) | 8 | — | — | — | Euthanized |
| EP/saline (Con−) | 8 | Ligatures, Saline | Remove Ligatures, Saline | Saline | Euthanized |
| EP/PF127 | 8 | Ligatures, PF127 | Remove Ligatures, PF127 | PF127 | Euthanized |
| EP/BIO | 8 | Ligatures, BIO | Remove Ligatures, BIO | BIO | Euthanized |
| EP/F127-BIO | 8 | Ligatures, F127-BIO | Remove, Ligatures, F127-BIO | F127-BIO | Euthanized |
| EP/PF127-BIO | 8 | Ligatures, PF127-BIO | Remove Ligatures, PF127-BIO | PF127-BIO | Euthanized |

EP: Experimental Periodontitis.

Micro-computed Tomography (μ-CT) Analysis of Periodontal Bone

All palate samples (including all three molars) were evaluated for alveolar bone quality using a high-resolution X-ray microtomography system (Skyscan 1172, Bruker, Kontich, Belgium), references to previous studies[32, 38]. The X-ray source was set as follows: 70 kV and 141 μA, resolution 12.9 μm, exposure time 1880 ms, and aluminum filter 0.5 mm-thick. To generate 3D images, scanning raw data were reconstructed using NRecon software. Sagittal sections were generated using CT-Analyzer software. To evaluate bone erosion, the distance from cementoenamel junction (CEJ) to alveolar bone crest (ABC) was determined using Skyscan Data viewer software. A longer distance from CEJ to ABC suggests more bone loss. For the analysis of histomorphometric parameters, such as bone volume (BV) and trabecular thickness (Tb.Th), a polygonal region of interest (ROI) between M1 and M2 was identified. The ROI was determined from the distopalatal of M1 to the mesiopalatal of M2 (length), 130 slices below the CEJ of M1 and M2 (height), and from the palatal side to the buccal side of M1 and M2 (width).

As described previously[39], femurs of these tested rats were also collected and scanned to assess the potential systemic effect of BIO. The X-ray source was set as the follows: voltage was 70 kV, current was 141 μA, exposure time was 700 ms, resolution was 8.6 μm, and aluminum filter was 0.5 mm-thick. The 3-D imagine were generated using the Skyscan NRecon and Skyscan DataViewer software. For bone quality analysis, a consistent polygonal ROI of trabecular bone at the distal femur was selected and the ROI was determined from 20 slices to 100 slices proximal to the growth plate. The bone histomorphometric parameters, including mean bone volume (BV), bone volume/tissue volume (BV/TV), trabecular thickness (Tb.Th) and bone mineral density (BMD) were determined using CT-Analyzer software.

Histological Analysis

At the completion of the μ-CT scanning, palates were decalcified for two weeks using 14% EDTA solution. Following decalcification, tissues were embedded in paraffin to obtain 4 μm thick sagittal sections. The slides were hematoxylin and eosin (H&E) stained for microscopic observation. To probe the presence of inflammatory cells between M1 and M2 and osteoclasts in the alveolar crest, a pathologist (SML) blind to experimental group assignment, evaluated the slides semi-quantitatively using an Olympus BX53 microscope. A semi-quantitative scoring system[32, 40, 41] was used to evaluate inflammatory cells, where 0 is negative, 1 is less than 30% of the affected tissues, 2 is some inflammatory cells (30-60%), and 3 is many inflammatory cells (>60%). Similarly, osteoclasts on the alveolar crest were evaluated using a semi-quantitative scoring system[32,42] where 0 is negative, 1 is a few osteoclasts lining less than 5% of alveolar bone surface, 2 is some osteoclasts (5-25%), and 3 is many osteoclasts (25-50%). Immunohistochemical (IHC) staining of β-catenin was performed using primary antibody (rabbit monoclonal anti-β-catenin antibody, Abcam, ab32572; 1:400 dilution). After deparaffinization and rehydration, sections were incubated in citrate buffer (pH=6.0, 0.1 M) for antigen retrieval, washed, and then incubated in hydrogen peroxide. Sections were then blocked and incubated with the primary antibody, followed by incubation with the secondary antibody. The antibody complexes were visualized using the DAB chromogen. Hematoxylin was used for counterstaining. The staining intensity was independently evaluated by a pathologist (SML) using a scale of from 0 to 3, where 0 is negative, 1 is weak staining, 2 is moderate staining, and 3 is strong staining[19, 43]. SML's scoring was calibrated by another examiner (YA) who evaluated a stack of slides and then compared with the SML's scores.

Statistical Analysis

All the generated data were expressed as the mean±SD (standard deviation). Statistical analyses were carried out using Prism 8.0 software (GraphPad, San Diego, CA). The Analysis of Variance (ANOVA) was used to analyze continuous outcomes among more than three groups. Tukey's pairwise post-hoc testing was performed for multiple comparisons. P-value<0.05 was considered statistically significant.

Results

Hydrogel Binding to Hydroxyapatite (HA)

Figure 2:
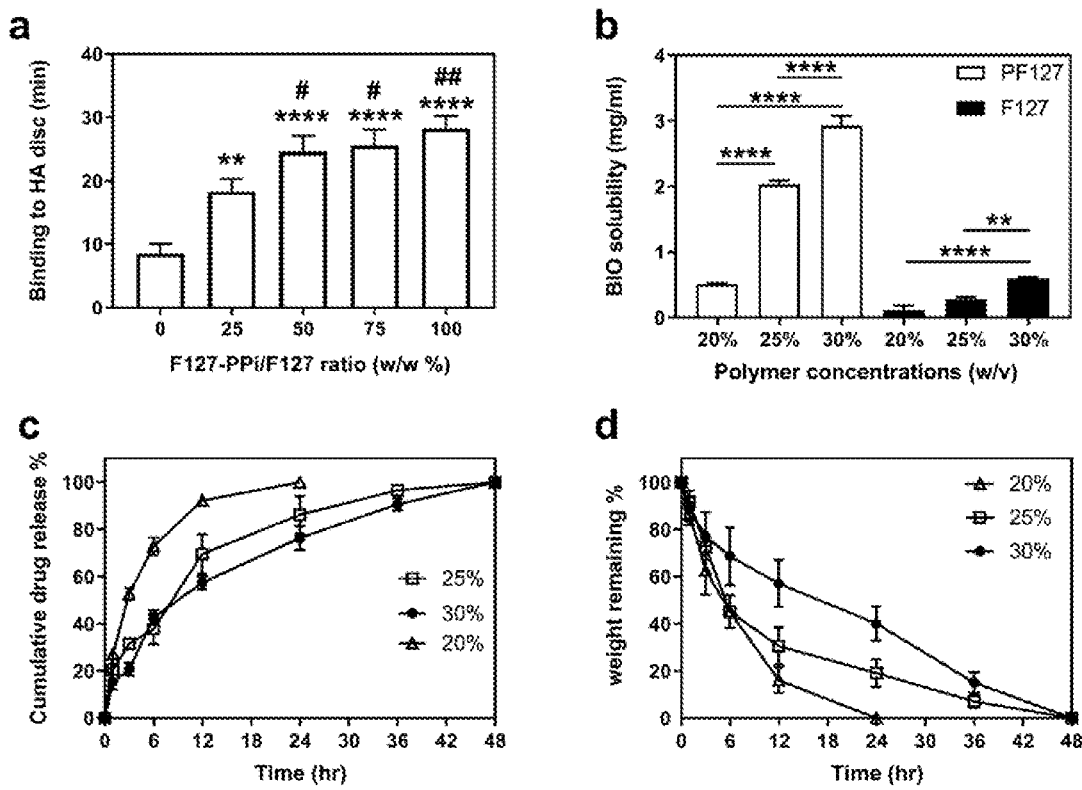
FIG. 2 shows in vitro characterization of PF127 hydrogels. (a) Assessment of hydroxyapatite (HA) binding of 25% w/v PF127 hydrogels prepared with different ratio of F127-PPi and F127. $P<0.01$, and $P<0.0001$ when compared to F127 hydrogel (ratio of 0); #$P<0.05$ and ##$P<0.01$ when compared to ratio of 25 (one-way ANOVA with Tukey's multiple comparisons). (b) Solubility of BIO in PF127 vs F127 solutions at 4° C. $P<0.01$ and ****$P<0.0001$ (one-way ANOVA with Tukey's multiple comparisons). (c) Cumulative BIO release from PF127 hydrogels at 37° C. (d) Erosion time of PF127 hydrogels incubated at 37° C. measured by weight remaining (%). Values are presented as the mean±SD, n=3.

The in vitro binding of the PF127 hydrogel (25% w/v) to HA was analyzed to predict their affinity to bone in vivo. As shown in FIG. 2a, the binding time increased as the F127-PPi content was increased in the hydrogel. Among different ratios of F127-PPi, 50, 75, and 100 (w/w %) showed the longest binding time to HA disc (24.6, 25.6, and 28.2 min), respectively. Their binding time was statistically significant when compared to F127 hydrogel (P<0.0001). The ratio of 25 (w/w %) also exhibited considerable binding time (18.2 min) which was significantly higher than F127 hydrogel (P<0.01). F127 hydrogel had the lowest binding time (8.5 min) among all the formulations. Based on this observation, the formulation of 50:50% w/w ratio of F127-PPi and F127 was used in the subsequent experiments as it showed strong binding affinity with relatively low PPi content.

Solubility of BIO in PF127 vs F127

The solubility of BIO in PF127 and F127-containing solutions of different concentrations was analyzed and compared at 4° C. with solution pH=7. As shown in FIG. 2b, the solubility of BIO appears to be proportionally dependent upon polymer concentration. The solubility of BIO in 20% PF127 was determined to be 0.5 mg/mL when compared to the 0.1 mg/mL in 20% F127. Furthermore, when polymer concentration was increased to 25%, BIO's solubility in PF127 was greatly improved to 2 mg/mL, while the value was only improved to 0.3 mg/mL in F127 solution. When concentration further increased to 30%, solubility in PF127 continued to increase to 3 mg/mL, while in F127 improved to 0.6 mg/mL. Clearly, PF127 can significantly improve BIO's aqueous solubility.

In vitro Release of BIO from PF127 Hydrogel

The releasing kinetics of BIO from PF127 hydrogels (20, 25, and 30% w/v) was studied at 37° C. As shown in FIG. 2c, the releasing kinetics of BIO from the hydrogels were found to be dependent upon the concentration of polymers: the higher the polymer concentration, the slower the release rate. The total release (~99%) of BIO from 20% w/v hydrogel occurred in 24 hr with burst release (~50%) in the first 3 hr. BIO release from 25% w/v hydrogel was shown with a burst release in the first 12 hr followed by a sustained release in the next 48 hr. For 30% w/v hydrogel, the release of BIO was sustained for over 48 hr.

In Vitro Hydrogel Erosion

The PF127 hydrogels erosion behavior was characterized by measuring weight remaining (%) at regular incubation time intervals. The results correlate with the release study and shown to be a function of the concentration of hydrogel. As shown in FIG. 2d, the hydrogel with 20% w/v concentration was completely eroded within 24 hr, ~50% was eroded in the first 3 hr. While 25% w/v hydrogel was completed eroded in 48 hr, ~60% weight loss was observed in the first 6 hr (burst erosion) followed by sustained erosion. Hydrogel with 30% w/v concentration was completely eroded in 48 hr in a sustained erosion manner.

Biocompatibility of PF127-Based Hydrogel

Figure 3:
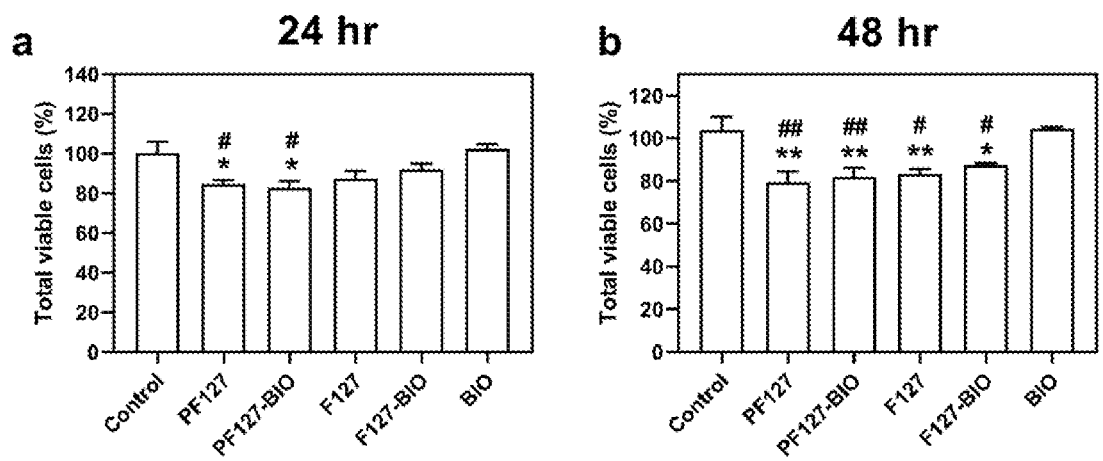
FIG. 3 shows effect of different treatments on growth of MC3T3-E1 cells measured by CCK-8 assay following (a) 24 hr and (b) 48 hr exposure. Data are shown as the mean± SD. *$P<0.05$ when compared to control group. #$P<0.05$ when compared to BIO group. **$P<0.01$ when compared to control group. ##$P<0.01$ when compared to BIO group.

To assess the safety of PF127 hydrogel comparing to F127 which is known to be biocompatible, mouse osteoblast MC3T3-L1 cells were treated with PF127, PF127-BIO, F127 and F127-BIO culture media extracts, or free BIO (100 nM) for 24 hr and 48 hr, and cell viability was defined using the CCK-8 assay (FIG. 3). The viability percentage of MC3T3-L1 cells treated with PF127 25% w/v, when compared to media-treated control, was slightly reduced to 84.5% after 24 hr and further decreased to 79.5% after 48 hr. The viability of MC3T3-L1 cells treated with F127 extract was 87.5% and 83.5% after 24 and 48 hr, respectively. When BIO was added to hydrogels, cell viability was not changed significantly. However, when cells treated with 100 nM of free BIO, the viability was determined to be 102% and 104.5% comparing to media-treated control.

Gelation and Viscosity Analysis of the PF127 Hydrogel

Figure 4:
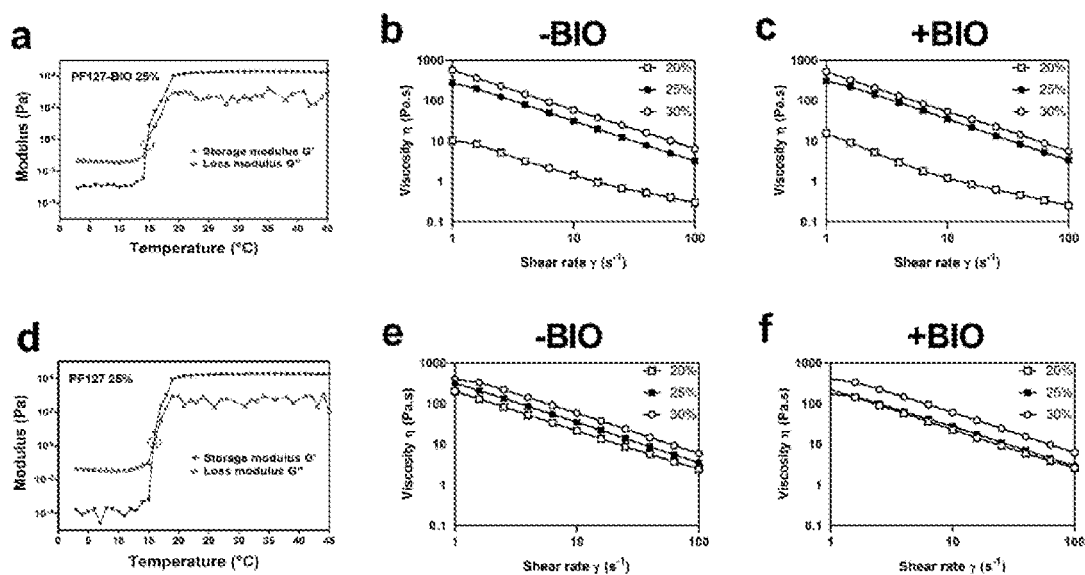
FIG. 4 shows physical properties of hydrogels. (a&d) Storage and loss modulus (G' and G'') that determined gelation temperature ($T_{gel}$) values of PF127-BIO and PF127 hydrogels. The viscosity of (b) PF127 and (c) PF127-BIO hydrogels at different shear rates. The viscosity of (e) F127 and (f) F127-BIO hydrogels at different shear rates.

Gelation temperature ($T_{gel}$) was determined based on the temperature sweep measurements of storage and loss modulus, G' and G" (FIG. 4). Samples showed fluid-like behaviors at low temperature ($T<T_{gel}$) because G' was much smaller than G". As samples were heated, both G' and G" increased sharply near $T_{gel}$, and G' became larger than G" at high temperature ($T>T_{gel}$), which shows that samples underwent gelation and demonstrated solid-like behaviors. Therefore, $T_{gel}$ was determined according to the cross-point between the G' and G" curves, and Table 2 summarizes the $T_{gel}$ values obtained.

TABLE 3

| Concentration (w/v) | F127 | PF127 | F127-BIO | PF127-BIO |
|---|---|---|---|---|
| 20% | 18.0 | 19.0 | 19.0 | 19.0 |
| 25% | 16.0 | 15.0 | 14.0 | 14.0 |
| 30% | 13.0 | 12.1 | 11.1 | 11.0 |

Viscosity measurements were also performed on PF127 and F127 hydrogels with and without BIO at 37° C. to study the effect of the pyrophosphorolation and drug content on their viscous property (FIG. 4). All hydrogels showed a typical shear-thinning behavior (non-Newtonian) and the viscosity decreased as a function of shear rate. No notable differences in viscosity were observed between PF127 and F127 hydrogels within the same concentration, except 20% w/v PF127 which showed low viscosity and forms a very weak hydrogel. BIO addition seemed to have no significant impact on hydrogels' viscous property.

Micro-computed Tomography (μ-CT) Analysis of the Periodontal Bone

Figure 5:
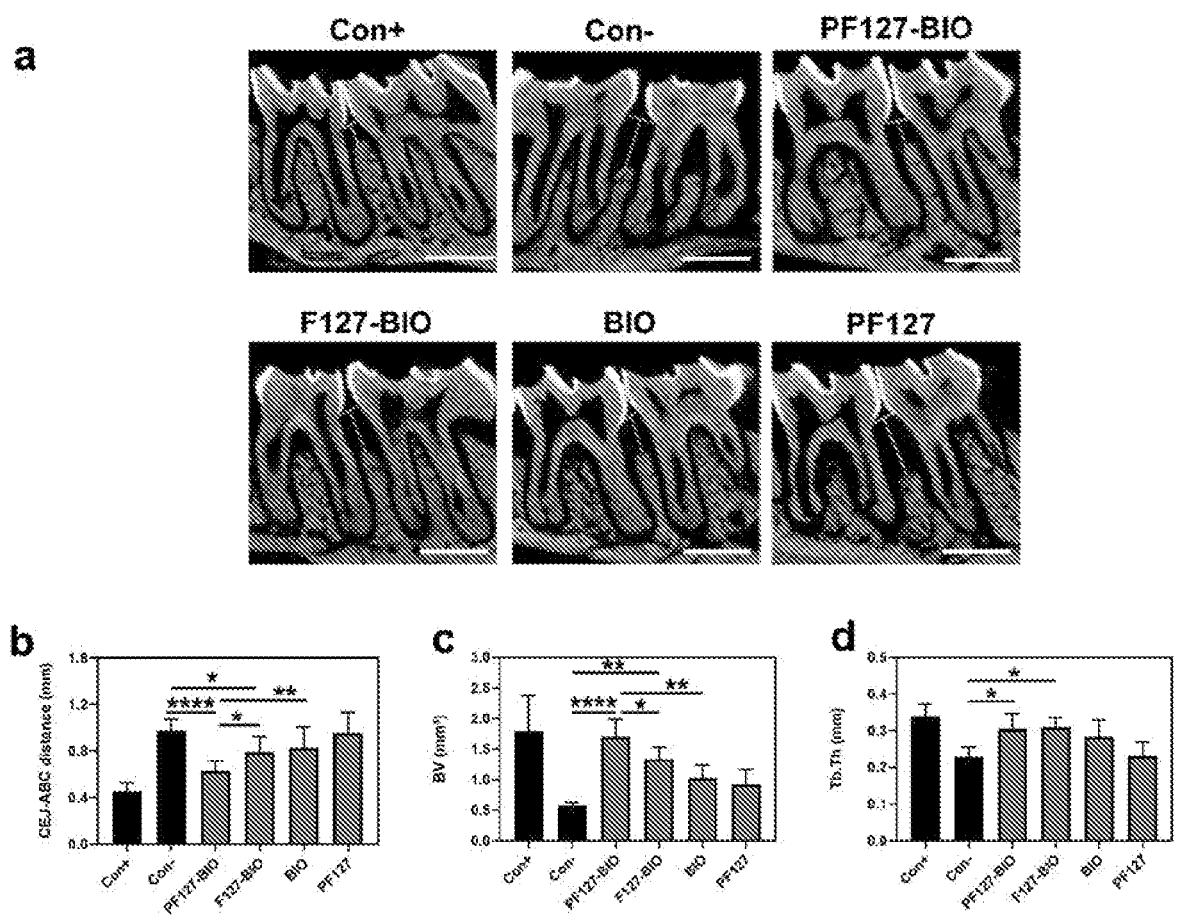
FIG. 5 shows the in vivo evaluation of PF127-BIO hydrogel's therapeutic efficacy in an experimental periodontitis rat model. (a) Micro-CT sagittal images showing the effect of different treatments on maxillary molar cementoenamel junction (CEJ) to alveolar bone crest (ABC). White vertical lines indicate ABC-CEJ distance. Scale bar=1 mm. (b) Measurement of the linear distance between CEJ and ABC. (c-d) Quantitative analysis of alveolar bone quality after different treatments. Bone volume (BV), trabecular thickness (Tb.Th). Values are presented as the mean± SD. *$P<0.05$, $P<0.01$, and **$P<0.0001$ (one-way ANOVA with Tukey's multiple comparisons).

As presented in FIG. 5a, it is evident that the PF127-BIO hydrogel prevented alveolar bone loss compared to the other treatments. The linear measurement (CEJ to ABC) indicated that the PF127-BIO hydrogel-treated group had the shortest distance among all other treated groups. While F127-BIO treated group exhibited statistically significant difference only when compared to the saline-treated group, free BIO-treated group did not show a statistically significant difference comparing to the saline-treated group (FIG. 5b). Bone volume (BV, FIG. 5c) and trabecular thickness (Tb.Th, FIG. 5d) were also quantified to further validate bone quality. The value of BV for the PF127-BIO treated group was significantly higher when compared to all the other treated groups. In contrast, F127-BIO treated group exhibited a statistically significant difference only when compared to the saline-treated group. The values of Tb. Th for the PF127-BIO and F127-BIO treated groups were significantly higher when compared to the saline group. No statistically significant difference between Free BIO treated group and the saline group was observed in the above μ-CT parameters. 3-D movies showing the periodontal bone quality after different treatments can be found in Supporting Information. Femur analyses data did not show any significant difference among all treatment groups.

Histological Evaluation

Figure 6:
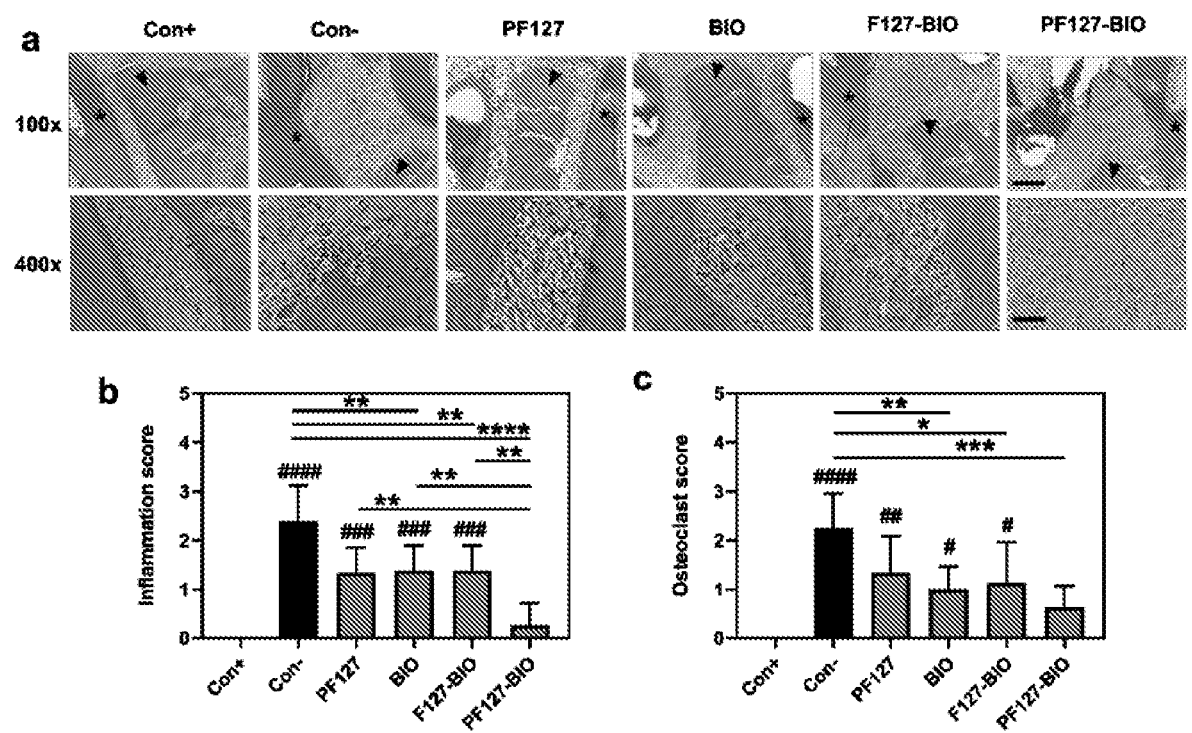
FIG. 6 shows histological analysis of papillary connective tissue and alveolar bone between first molar (M1) and second molar (M2) after three weeks of different treatments. (a) Representative images from different treatment groups of H&E stained tissues. Semi-quantitative assessment of (b) inflammatory cells and (c) osteoclasts. Values are presented as the mean±SD. *$P<0.05$, $P<0.01$, *$P<0.001$, and ****$P<0.0001$. #$P<0.05$, ##$P<0.01$, ###$P<0.001$, and ####$P<0.0001$ when compared to Con+ group. (one-way ANOVA). Scale bar=200 μm and 50 μm for 100× and 400×, respectively. Black arrows indicate alveolar bone and asterisks indicate first molar (M1).
Figure 7:
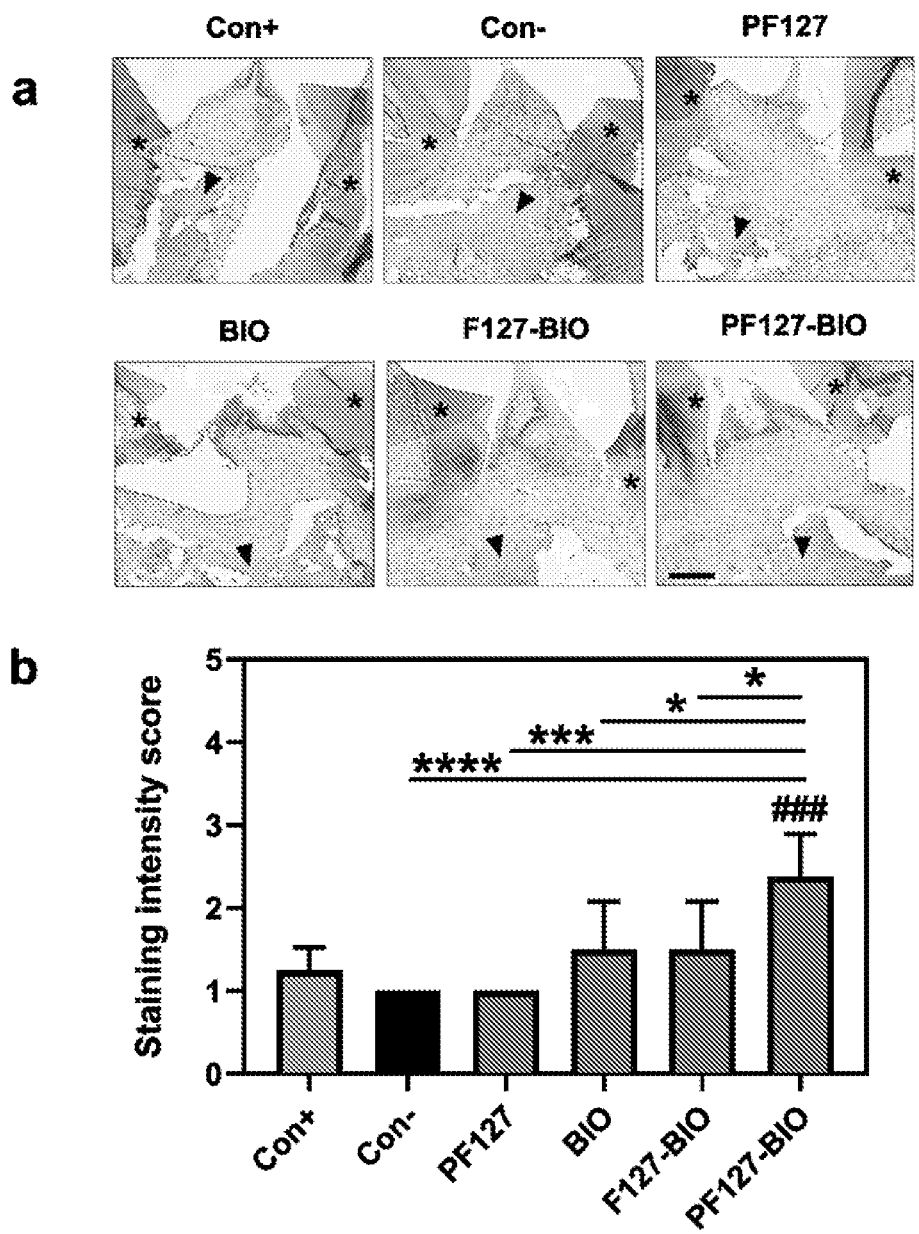
FIG. 7 shows immunohistochemistry (IHC) analysis of β-catenin at the treatment area. (a) Representative images from different treatment groups of IHC staining of β-catenin of connective tissue above the alveolar bone crest (ABC) and between first molar (M1) and second molar (M2). (b) Semi-quantitative assessment of β-catenin positive cells interproximally between first molar (M1) and second molar (M2). Values are presented as the mean±SD. *P<0.05, P<0.01, *P<0.001, and ****P<0.0001. ####P<0.001 when compared to Con+ group. (one-way ANOVA). Scale bar=200 μm. Black arrows indicate alveolar bone and asterisks indicate first molar (M1) and second molar (M2).

To study the impacts of different treatment on inflammatory cells, osteoclasts, and β-catenin, images of stained tissue sections (FIGS. 5a, 6a) were assessed semi-quantitatively. Histology scores of inflammatory cells were shown in FIG. 6b. As expected, healthy Con+ group has a score of 0 for both inflammatory cells and osteoclasts, which is significantly lower than all the treatment groups except PF127-BIO group. There is no statistically significant difference between healthy Con+ and PF127-BIO group. PF127-BIO hydrogel-treated group has the lowest inflammatory cell score when compared to all the other groups (P<0.0001 compared to saline Con-group, P<0.01 compared to F127-BIO and free BIO treated groups), while F127-BIO and free BIO treated groups exhibited a statistically significant difference (P<0.01) only when compared to the saline Con-group. PF127-BIO hydrogel treated group had the lowest osteoclast score comparing to all treatment groups except healthy Con+ group and was significantly (P<0.001) lower than that of the saline Con-group (FIG. 6c). Scores of F127-BIO and free BIO treated groups were significantly lower than the saline Con-group. β-Catenin positive cell score of the PF127-BIO hydrogel-treated group was the highest among all treatment groups (FIG. 7b, P<0.0001 compared to saline Con-group, P<0.05 compared to F127-BIO and free BIO treated groups, P<0.001 when compared to healthy Con+ group). Scores of F127-BIO and free BIO-treated groups were not significantly different (P>0.05) from the saline Con-, PF127, and healthy Con+ group.

Example 2

In this example, simvastatin (SIM) was used as the therapeutic agent. The preparation of PF127 was described in Example 1.

Preparation of SIM-Loaded PF127/F127 Hydrogel

Film hydration method: An excess amount of SIM was dissolved in methanol solution of PF127/F127. Methanol was evaporated to form a film and then on the following day hydration was done with iced water for 30 min to prevent formation of gel. Free drug was removed after centrifugation.

Solvent evaporation method: PF127/F127 and SIM were dissolved in acetone and then added dropwise to iced water with stirring. Acetone was evaporated overnight. Free drug was removed after centrifugation.

Direct dissolution method: Iced PF127/F127 solution was prepared first and an excess amount of SIM was added and mixed for 48 hr. Free drug was removed after centrifugation.

Results are shown in Table 3. Based upon this result direct dissolution method was used in the preparation of the SIM-loaded PF127/F127 hydrogel.

TABLE 4

| Preparation Method | SIM EE (%) | Particle Size (nm) | PDI |
| --- | --- | --- | --- |
| Direct Dissolution | 40.3 ± 5.5 | 34.32 | 0.147 |
| Solvent Evaporation | 36.2 ± 5.5 | 53.4 | 0.136 |
| Film Hydration | 66.5 ± 4.8 | 20.62 | 0.335 |

Figure 8:
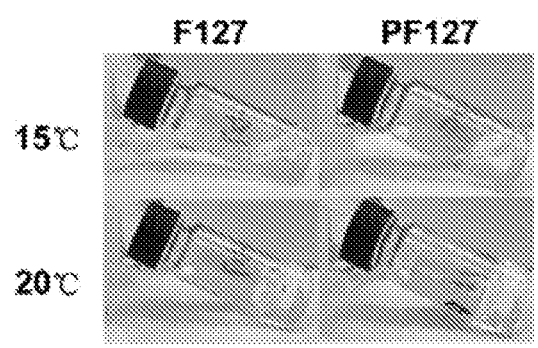
FIG. 8 shows images of the phase transition of SIM-loaded PF127/F127 hydrogel.

Phase transition of SIM-loaded PF127/F127 hydrogel is shown in FIG. 8. The result suggests that the pyrophosphorylation of F127 does not affect its thermoresponsive behavior.

Animal Study on Therapeutic Efficacy in Periodontitis

The experimental process is described in Example 1. The grouping and treatment are shown in Table 4.

| Group | Number | Side | Week 0 | Week 1 | Week 2 | Week 3 |
| --- | --- | --- | --- | --- | --- | --- |
| 1 | 5 | Left | Place ligature, F127 treatment | Remove ligature, F127 treatment | F127 treatment | Euthanasia |
|  |  | Right | Place ligature, SIM-loaded F127 treatment | Remove ligature, SIM-loaded F127 treatment | SIM-loaded F127 treatment |  |
| 2 | 5 | Left | Place ligature, Free SIM treatment | Remove ligature, Free SIM treatment | Free SIM treatment | Euthanasia |
|  |  | Right | Place ligature, SIM-loaded PF127 treatment | Remove ligature, SIM-loaded PF127 treatment | SIM-loaded PF127 treatment |  |
| 3 | 5 | Left | Place ligature, PF127 treatment | Remove ligature, PF127 treatment | PF127 treatment | Euthanasia |
|  |  | Right | Place ligature, Saline treatment | Remove ligature, Saline treatment | Saline treatment |  |

Figure 9:
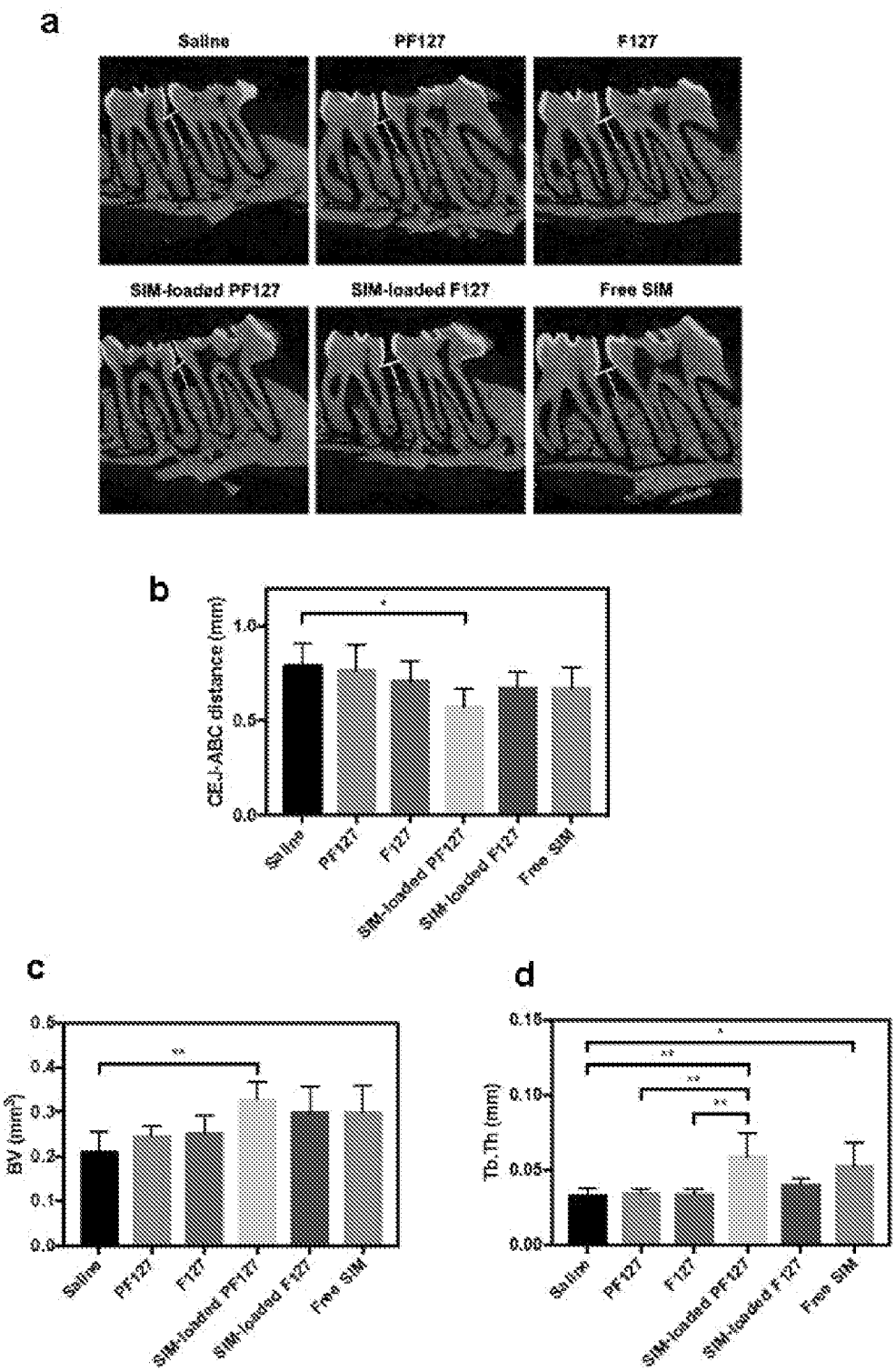
FIG. 9 shows the in vivo evaluation of SIM-loaded PF127 hydrogel's therapeutic efficacy in an experimental periodontitis rat model. (a) Micro-CT sagittal images showing the effect of different treatments on maxillary molar cementoenamel junction (CEJ) to alveolar bone crest (ABC). White vertical lines indicate ABC-CEJ distance. Scale bar=1 mm. (b) Measurement of the linear distance between CEJ and ABC. (c-d) Quantitative analysis of alveolar bone quality after different treatments. Bone volume (BV), trabecular thickness (Tb.Th). Values are presented as the mean±SD. *P<0.05, **P<0.01 (one-way ANOVA with Tukey's multiple comparisons).

As shown in FIG. 9, SIM-loaded PF127 formulation is the only formulation that can significantly reduce the CEJ-ABC distance when compared to saline control. In addition, the treatment can also significantly increase the periodontal bone volume (BV) and trabecular thickness (Tb.Th).

REFERENCES

[1] Pihlstrom B L, Michalowicz B S, Johnson N W. Periodontal diseases. The Lancet. 2005 November; 366 (9499):1809-1820.

[2] Herrera D, Sanz M, Jepsen S, Needleman I, Roldán S. A systematic review on the effect of systemic antimicrobials as an adjunct to scaling and root planing in periodontitis patients. Journal of Clinical Periodontology. 2002 December; 29:136-159.

[3] Greenstein G. Local drug delivery in the treatment of periodontal diseases: assessing the clinical significance of the results. Journal of Periodontology. 2006 April; 77(4): 565-578.

[4] Williams R C, Jeffcoat M K, Howell T H, Reddy M S, Johnson H G, Hall C M, Goldhaber P. Ibuprofen: an inhibitor of alveolar bone resorption in beagles. Journal of Periodontal Research. 1988 July; 23 (4):225-229.

[5] Raja S, Byakod G, Pudakalkatti P. Growth factors in periodontal regeneration. International Journal of Dental Hygiene. 2009 May; 7(2):82-89.

[6] Wang H, Brown J, Martin M. Glycogen synthase kinase 3: a point of convergence for the host inflammatory response. Cytokine. 2011 February; 53(2):130-140.

[7] Huang W C, Lin Y S, Wang C Y, Tsai C C, Tseng H C, Chen C L, Lu P J, Chen P S, Qian L, Hong J S, Lin C F. Glycogen synthase kinase-3 negatively regulates anti-inflammatory interleukin-10 for lipopolysaccharide-induced iNOS/NO biosynthesis and RANTES production in microglial cells. Immunology. 2009 September; 128(1 Pt 2):c275-c286.

[8] Whittle B J, Varga C, Pósa A, Molnár A, Collin M, Thiemermann C. Reduction of experimental colitis in the rat by inhibitors of glycogen synthase kinase-3β. British Journal of Pharmacology. 2006 March; 147(5):575-582.

[9] Arioka M, Takahashi-Yanaga F, Sasaki M, Yoshihara T, Morimoto S, Hirata M, Mori Y, Sasaguri T. Acceleration of bone regeneration by local application of lithium: Wnt signal-mediated osteoblastogenesis and Wnt signal-independent suppression of osteoclastogenesis. Biochemical Pharmacology. 2014 August; 90(4):397-405.

[10] Martinez A, Castro A, Dorronsoro I, Alonso M. Glycogen synthase kinase 3 (GSK-3) inhibitors as new promising drugs for diabetes, neurodegeneration, cancer, and inflammation. Medicinal Research Reviews. 2002 July; 22 (4): 373-384.

[11] Adamowicz K, Wang H, Jotwani R, Zeller I, Potempa J, Scott D A. Inhibition of GSK3 abolishes bacterial-induced periodontal bone loss in mice. Molecular Medicine. 2012 August; 18(8):1190-1196.

[12] Xie J, Méndez J D, Méndez-Valenzuela V, Aguilar-Hernández M M. Cellular signalling of the receptor for advanced glycation end products (RAGE). Cellular Signaling. 2013 November; 25(11):2185-2197.

[13] Sanguineti R, Storace D, Monacelli F, Federici A, Odetti P. Pentosidine effects on human osteoblasts in vitro. Annals of the New York Academy of Sciences. 2008 April; 1126(1):166-172.

[14] Wang F S, Ko J Y, Weng L H, Yeh D W, Ke H J, Wu S L. Inhibition of glycogen synthase kinase-3β attenuates glucocorticoid-induced bone loss. Life Sciences. 2009 November; 85(19-20):685-692.

[15] Krause U, Harris S, Green A, Ylostalo J, Zeitouni S, Lee N, Gregory C A. Pharmaceutical modulation of canonical Wnt signaling in multipotent stromal cells for improved osteoinductive therapy. Proceedings of the National Academy of Sciences. 2010 March; 107(9): 4147-4152.

[16] Fukuda T, Kokabu S, Ohte S, Sasanuma H, Kanomata K, Yoneyama K, Kato H, Akita M, Oda H, Katagiri T. Canonical Wnts and BMPs cooperatively induce osteoblastic differentiation through a GSK3β-dependent and β-catenin-independent mechanism. Differentiation. 2010 July; 80(1):46-52.

[17] Piters E, Boudin E, Van Hul W. Wnt signaling: a win for bone. Archives of Biochemistry and Biophysics. 2008 May; 473(2):112-116.

[18] Kwon Y J, Yoon C H, Lec S W, Park Y B, Lee S K, Park M C. Inhibition of glycogen synthase kinase-3β suppresses inflammatory responses in rheumatoid arthritis fibroblast-like synoviocytes and collagen-induced arthritis. Joint Bone Spine. 2014 May; 81(3):240-246.

[19] Jiang Y Y, Wen J, Gong C, Lin S, Zhang C X, Chen S, Cheng W, Li H. BIO alleviated compressive mechanical force-mediated mandibular cartilage pathological changes through Wnt/β-catenin signaling activation. Journal of Orthopaedic Research. 2018 April; 36(4):1228-1237.

[20] Neves V C, Babb R, Chandrasekaran D, Sharpe P T. Promotion of natural tooth repair by small molecule GSK3 antagonists. Scientific Reports. 2017 January; 7:39654.

[21] Takahashi-Yanaga F. Activator or inhibitor? GSK-3 as a new drug target. Biochemical Pharmacology. 2013 July; 86(2):191-199.

[22] Kahn M. Can we safely target the WNT pathway? Nature Reviews Drug Discovery. 2014 July; 13(7):513-532.

[23] Huang P, Yan R, Zhang X, Wang L, Ke X, Qu Y. Activating Wnt/β-catenin signaling pathway for disease therapy: Challenges and opportunities. Pharmacology & Therapeutics. 2019 April; 196:79-90.

[24] Giuliano E, Paolino D, Fresta M, Cosco D. Mucosal Applications of Poloxamer 407-Based Hydrogels: An Overview. Pharmaceutics. 2018 September; 10(3):E159.

[25] Dumortier G, Grossiord J L, Agnely F, Chaumeil J C. A review of poloxamer 407 pharmaceutical and pharmacological characteristics. Pharmaceutical Research. 2006 December; 23(12):2709-2728.

[26] Fakhar-ud-Din, Khan G M. Development and characterisation of levosulpiride-loaded suppositories with improved bioavailability in vivo. Pharmaceutical Development and Technology. 2019 January; 24 (1):63-69.

[27] Monti D, Burgalassi S, Rossato M S, Albertini B, Passerini N, Rodriguez L, Chetoni P. Poloxamer 407 microspheres for orotransmucosal drug delivery. Part II: In vitro/in vivo evaluation. International Journal of Pharmaceutics. 2010 November; 400(1-2):32-36.

[28] Rangabhatla A S, Tantishaiyakul V, Boonrat O, Hirun N, Ouiyangkul P. Novel in situ mucoadhesive gels based on Pluronic F127 and xyloglucan containing metronidazole for treatment of periodontal disease. Iranian Polymer Journal. 2017 November; 26(11):851-859.

[29] Akash M S, Rchman K, Li N, Gao J Q, Sun H, Chen S. Sustained delivery of IL-1Ra from pluronic F127-based thermosensitive gel prolongs its therapeutic potentials. Pharmaceutical Research. 2012 Dec. 1; 29(12): 3475-3485.

[30] Diniz. I M, Chen C, Xu X, Ansari S, Zadch H H, Marques M M, Shi S, Moshaverinia A. Pluronic F-127 hydrogel as a promising scaffold for encapsulation of dental-derived mesenchymal stem cells. Journal of Materials Science: Materials in Medicine. 2015 March; 26(3): 153.

[31] Polychronopoulos P, Magiatis P, Skaltsounis A L, Myrianthopoulos V, Mikros E, Tarricone A, Musacchio A, Roe S M, Pearl L, Leost M, Greengard P. Structural basis for the synthesis of indirubins as potent and selective inhibitors of glycogen synthase kinase-3 and cyclin-dependent kinases. Journal of Medicinal Chemistry. 2004 February; 47(4):935-946.

[32] Wang X, Jia Z, Almoshari Y, Lele S M, Reinhardt R A, Wang D. Local application of pyrophosphorylated simvastatin prevents experimental periodontitis. Pharmaceutical Research. 2018 August; 35(8):164.

[33] Deshmukh M, Singh Y, Gunaseelan S, Gao D, Stein S, Sinko P J. Biodegradable poly(ethylene glycol) hydrogels based on a self-climination degradation mechanism. Biomaterials. 2010 September; 31(26):6675-6684.

[34] Li Y, Cao J, Han S, Liang Y, Zhang T, Zhao H, Wang L, Sun Y. ECM based injectable thermo-sensitive hydrogel on the recovery of injured cartilage induced by osteoarthritis. Artificial Cells, Nanomedicine, and Biotechnology. 2018 November; 46(sup2):152-160.

[35] Ma X, He Z, Han F, Zhong Z, Chen L, Li B. Preparation of collagen/hydroxyapatite/alendronate hybrid hydrogels as potential scaffolds for bone regeneration. Colloids and Surfaces B: Biointerfaces. 2016 July; 143:81-87.

[36] Winter H H. Can the gel point of a cross-linking polymer be detected by the G'-G" crossover? Polymer Engineering and Science. 1987 December; 27(22):1698-1702.

[37] Bercea M, Daric R N, Nita L E, Morariu S. Temperature Responsive Gels Based on Pluronic F127 and Poly(vinyl

[38] Bradley A D, Zhang Y, Jia Z, Zhao G, Wang X, Pranke L, Schmid M J, Wang D, Reinhardt R A. Effect of simvastatin prodrug on experimental periodontitis. Journal of Periodontology. 2016 May; 87(5):577-582.
[39] Jia Z, Wang X, Wei X, Zhao G, Foster K W, Qiu F, Gao Y, Yuan F, Yu F, Thiele G M, Bronich T K, O'Dell, J R, Wang D. Micelle-Forming Dexamethasone Prodrug Attenuates Nephritis in Lupus-Prone Mice without Apparent Glucocorticoid Side Effects. ACS Nano. 2018 July; 12(8):7663-7681.
[40] Gibson-Corley K N, Olivier A K, Meyerholz D K. Principles for valid histopathologic scoring in research. Veterinary Pathology. 2013 November; 50(6):1007-1015.
[41] Schett G, Stolina M, Bolon B, Middleton S, Adlam M, Brown H, Zhu L, Feige U, Zack D J. Analysis of the kinetics of osteoclastogenesis in arthritic rats. Arthritis & Rheumatism: Official Journal of the American College of Rheumatology. 2005 October; 52(10):3192-3201.
[42] Bolon B, Morony S, Cheng Y, Hu Y L, Feige U. Osteoclast numbers in Lewis rats with adjuvant-induced arthritis: identification of preferred sites and parameters for rapid quantitative analysis. Veterinary Pathology. 2004 January; 41(1):30-36.
[43] Song S, Ajani J A, Honjo S, Maru D M, Chen Q, Scott A W, Heallen T R, Xiao L, Hofstetter W L, Weston B, Lee J H. Hippo coactivator YAP1 upregulates SOX9 and endows esophageal cancer cells with stem-like properties. Cancer Research. 2014 August; 74(15):4170-4182.
[44] Georgiou K R, King T J, Scherer M A, Zhou H, Foster B K, Xian C J. Attenuated Wnt/β-catenin signalling mediates methotrexate chemotherapy-induced bone loss and marrow adiposity in rats. Bone. 2012 June; 50(6): 1223-1233.
[45] Park D W, Jiang S, Liu Y, Siegal G P, Inoki K, Abraham E, Zmijewski J W. GSK3β-dependent inhibition of AMPK potentiates activation of neutrophils and macrophages and enhances severity of acute lung injury. American Journal of Physiology-Lung Cellular and Molecular Physiology. 2014 September; 307(10):L735-L745.
[46] Wang Y, Huang W C, Wang C Y, Tsai C C, Chen C L, Chang Y T, Kai J I, Lin C F. Inhibiting glycogen synthase kinase-3 reduces endotoxaemic acute renal failure by down-regulating inflammation and renal cell apoptosis. British Journal of Pharmacology. 2009 July; 157(6):1004-1013.
[47] Klamer G, Shen S, Song E, Rice A M, Knight R, Lindeman R, O'Brien T A, Dolnikov A. GSK3 inhibition prevents lethal GVHD in mice. Experimental Hematology. 2013 January; 41(1):39-55.
[48] Bai X, Gao M, Syed S, Zhuang J, Xu X, Zhang X Q. Bioactive hydrogels for bone regeneration. Bioactive Materials. 2018 December; 3(4):401-417.
[49] Chen F, Jia Z, Rice K C, Reinhardt R A, Bayles K W, Wang D. The development of dentotropic micelles with biodegradable tooth-binding moieties. Pharmaceutical Research. 2013 November; 30(11):2808-2817.
[50] Wang D, Miller S C, Kopečková P, Kopeček J. Bone-targeting macromolecular therapeutics. Advanced Drug Delivery Reviews. 2005 May; 57(7):1049-1076.
[51] Purcell P M, Boyd I W. Bisphosphonates and osteonecrosis of the jaw. Medical Journal of Australia. 2005 April; 182(8):417-418.
[52] Kennel K A, Drake M T. Adverse effects of bisphosphonates: implications for osteoporosis management. Mayo Clinic Proceedings 2009 July; 84(7):632-638.
[53] Shellis R P, Addy M, Rees G D. In vitro studies on the effect of sodium tripolyphosphate on the interactions of stain and salivary protein with hydroxyapatite. Journal of dentistry. 2005 Apr. 1; 33(4):313-24.
[54] Sharma P K, Bhatia S R. Effect of anti-inflammatories on Pluronic® F127: micellar assembly, gelation and partitioning. International Journal of Pharmaceutics. 2004 July; 278(2):361-377.
[55] Low S A, Galliford C V, Yang J, Low P S, Kopeček J. Biodistribution of fracture-targeted gsk3β inhibitor-loaded micelles for improved fracture healing. Biomacromolecules. 2015 September; 16(10):3145-3153.
[56] Jain, M. K. & Ridker, P. M. Anti-Inflammatory Effects of Statins: Clinical Evidence and Basic Mechanisms. Nature Reviews Drug Discovery, 2005, 4, p. 977-87.

The invention claimed is:

1. A drug delivery composition comprising a therapeutic agent and a mixture of a poloxamer and its corresponding pyrophosphorylated poloxamer,
wherein the poloxamer has the structure:

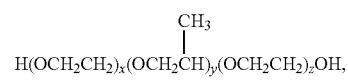

wherein x and z are 101 and y is 56;
wherein said pyrophosphorylated poloxamer has the structure:

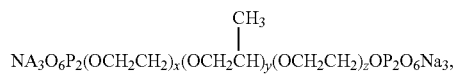

wherein x and z are 101 and y is 56; and
wherein the drug delivery composition is a thermoresponsive hydrogel.

2. The drug delivery composition of claim 1, wherein the therapeutic agent is selected from anti-inflammatory compounds, bone anabolic compounds, bone antiresorptive compounds, anti-cancer compounds, statins, and antimicrobial compounds.

3. The drug delivery composition of claim 1, wherein the therapeutic agent is a GSK3-beta inhibitor or a statin.

4. The drug delivery composition of claim 3, wherein the GSK3-beta inhibitor is selected from indirubin, lithium, zinc, beryllium, and mixtures thereof.

5. The drug delivery composition of claim 3, wherein the GSK3-beta inhibitor is 6-bromoindirubin-3'-oxime, lithium, or zinc.

6. The drug delivery composition of claim 3, wherein the statin is selected from atorvastatin, fluvastatin, lovastatin, pravastatin, rosuvastatin, simvastatin, pitavastatin, and mixtures thereof.

7. The drug delivery composition of claim 3, wherein the statin is simvastatin.

8. A method of manufacturing the drug delivery composition of claim 1, the method comprising:
subjecting the poloxamer to a tosylation reaction to synthesize a tosylated poloxamer;
subjecting the tosylated poloxamer to pyrophosphorylation to obtain a pyrophosphorylated poloxamer; and
dissolving the therapeutic agent in the pyrophosphorylated poloxamer to obtain a drug delivery composition.

9. The method according to claim 8, wherein the poloxamer is poloxamer 407 (Pluronic F127), and the therapeutic agent is a GSK3-beta inhibitor or a statin.

10. The method according to claim 8, wherein the drug delivery composition is an injectable solution, which can form a hydrogel upon in vivo instillation.

11. A method of treating an oral disease or condition, comprising administering the drug delivery composition of claim 1 in situ at a topical site to a subject in need thereof.

12. The method of claim 11, wherein the topical site is a periodontal pocket and the oral disease or condition is a dental disease or condition.

13. The method of claim 11, wherein the oral disease or condition is periodontitis.

14. The method of claim 11, wherein the composition is capable of releasing the therapeutic agent to treat the oral disease over a period of at least 2 days, and wherein the composition is only remained at the topical site.

15. The drug delivery composition of claim 1, wherein the ratio (w/w) of pyrophosphorylated poloxamer to poloxamer is 50:50.

16. The drug delivery composition of claim 1, wherein said mixture of a poloxamer and its corresponding pyrophosphorylated poloxamer is present from 20% to 35% w/v in said drug delivery composition.

17. The drug delivery composition of claim 15, wherein said mixture of a poloxamer and its corresponding pyrophosphorylated poloxamer is present from 20% to 35% w/v in said drug delivery composition.

18. The drug delivery composition of claim 16, wherein said mixture of a poloxamer and its corresponding pyrophosphorylated poloxamer is present from 25% to 35% w/v in said drug delivery composition.

19. The drug delivery composition of claim 18, wherein said mixture of a poloxamer and its corresponding pyrophosphorylated poloxamer is present from 25% to 30% w/v in said drug delivery composition.

* * * * *